US011439615B2

(12) United States Patent
Sivak et al.

(10) Patent No.: US 11,439,615 B2
(45) Date of Patent: Sep. 13, 2022

(54) LIPOXIN AND LIPOXIN ANALOGUE MEDIATED NEUROPROTECTION AND TREATMENTS

(71) Applicants: University Health Network, Toronto (CA); The Regents of the University of California, Oakland, CA (US)

(72) Inventors: Jeremy M. Sivak, Toronto (CA); Izhar Livne-Bar, Toronto (CA); John G. Flanagan, Berkeley, CA (US); Karsten Gronert, Walnut Creek, CA (US); Jessica Wei, Berkeley, CA (US)

(73) Assignees: University Health Network, Toronto (CA); The Regents of the University of California, Oakland, CA (US)

(*) Notice: Subject to any disclaimer, the term of this patent is extended or adjusted under 35 U.S.C. 154(b) by 245 days.

(21) Appl. No.: 16/492,494

(22) PCT Filed: Mar. 9, 2018

(86) PCT No.: PCT/CA2018/050288
§ 371 (c)(1),
(2) Date: Sep. 9, 2019

(87) PCT Pub. No.: WO2018/161175
PCT Pub. Date: Sep. 13, 2018

(65) Prior Publication Data
US 2021/0275484 A1     Sep. 9, 2021

Related U.S. Application Data

(60) Provisional application No. 62/469,396, filed on Mar. 9, 2017.

(51) Int. Cl.
*A61K 31/202* (2006.01)
*A61P 25/28* (2006.01)
*A61K 31/557* (2006.01)

(52) U.S. Cl.
CPC .......... *A61K 31/202* (2013.01); *A61K 31/557* (2013.01); *A61P 25/28* (2018.01)

(58) Field of Classification Search
None
See application file for complete search history.

(56) References Cited

U.S. PATENT DOCUMENTS

| | | |
|---|---|---|
| 4,560,514 A | 12/1985 | Samuelsson et al. |
| 5,441,951 A | 8/1995 | Serhan |
| 5,648,512 A | 7/1997 | Serhan |
| 5,650,435 A | 7/1997 | Madara et al. |
| 6,048,897 A | 4/2000 | Serhan |
| 6,627,658 B2 * | 9/2003 | Serhan ............... A61P 9/10 514/559 |
| 6,635,776 B2 | 10/2003 | Serhan |
| 6,645,978 B1 * | 11/2003 | Gamache ............. A61K 31/557 514/310 |
| 6,653,493 B2 | 11/2003 | Serhan |
| 6,670,396 B2 | 12/2003 | Serhan et al. |
| 6,750,360 B2 | 6/2004 | Serhan |
| 6,887,901 B1 | 5/2005 | Serhan |
| 7,288,569 B2 | 10/2007 | Serhan |
| 7,294,728 B2 | 11/2007 | Serhan |
| 7,700,650 B2 | 4/2010 | Van Dyke et al. |
| 7,741,369 B2 | 6/2010 | Serhan |
| 7,759,395 B2 | 7/2010 | Serhan et al. |
| 7,803,557 B2 | 9/2010 | Serhan et al. |
| 7,812,054 B2 | 10/2010 | Van Dyke et al. |
| 7,825,271 B2 | 11/2010 | Serhan |
| 7,872,152 B2 | 1/2011 | Serhan et al. |
| 7,994,219 B2 | 8/2011 | Serhan et al. |
| 8,008,282 B2 | 8/2011 | Serhan et al. |
| 8,093,417 B2 | 1/2012 | Van Dyke et al. |
| 8,119,691 B2 | 2/2012 | Serhan et al. |
| 8,273,792 B2 | 9/2012 | Serhan et al. |
| 8,569,542 B2 | 10/2013 | Serhan et al. |
| 8,604,229 B2 | 12/2013 | Van Dyke et al. |
| 8,722,654 B2 | 5/2014 | Serhan et al. |
| 8,846,733 B2 | 9/2014 | Bur et al. |
| 8,933,270 B2 | 1/2015 | Serhan et al. |
| 9,364,454 B2 | 6/2016 | Serhan et al. |
| 9,463,177 B2 | 10/2016 | Conte et al. |
| 2002/0076394 A1 | 6/2002 | Leone et al. |

(Continued)

FOREIGN PATENT DOCUMENTS

| CA | 2537865 A1 | 2/2005 |
|---|---|---|
| WO | 2009/051670 A2 | 4/2009 |

(Continued)

OTHER PUBLICATIONS

Karra et al (Nature 8(4):852-862, 2015) (Year: 2015).*
Mokhtari-Zaer et al (Brain Res Bull 165:40-47, 2020) (Year: 2020).*
Xiong et al (Curr Opin Investig Drugs 11(3):298-308, 2010) (Year: 2010).*
Atkins et al (Rev Neurol Dis 5(2):73-81, 2008) (Year: 2008).*
Murphy, R.C., et al. Electrospray ionization and tandem mass spectrometry of eicosanoids. Anal Biochem. 2005, 346 (1), 1-42.
Romano, M., et al. Lipoxins and aspirin-triggered lipoxins in resolution of inflammation. Eur J Pharmacol 2015, 760, 49-63.
Calkins, D. J., et al. The challenge of regenerative therapies for the optic nerve in glaucoma. Exp Eye Res. Jan. 2017; 157, 28-33.
Kaviarasan, K., et al. Low blood and vitreal BDNF, LXA4 and altered Th1/Th2 cytokine balance are potential risk factors for diabetic retinopathy. Metabolism. 2015, 64(9), 958-66.

(Continued)

*Primary Examiner* — Craig D Ricci
(74) *Attorney, Agent, or Firm* — Fitch Even Tabin & Flannery LLP

(57) ABSTRACT

Methods and compositions for inhibiting or preventing neurodegeneration, specifically hippocampal, cortical, and/or retinal ganglion cell neurons (RGC), and degeneration and/or cell loss or treating related disorders and diseases comprising administering to a subject an effective amount of one or more lipoxin compounds and/or lipoxin analogues such that degeneration and/or cell loss of neurons is inhibited or prevented.

17 Claims, 24 Drawing Sheets

(56) References Cited

U.S. PATENT DOCUMENTS

2005/0203184 A1* 9/2005 Petasis ............... A61K 45/06
554/61

FOREIGN PATENT DOCUMENTS

WO    WO 2009/051670    *    4/2009  ............ A61P 27/02
WO    2009/058815 A2    5/2009

OTHER PUBLICATIONS

Tham, Y. C., et al. Global prevalence of glaucoma and projections of glaucoma burden through 2040: a systematic review and meta-analysis. Ophthalmology. 2014, 121(11), 2081-90.
Das, U. N. Lipoxins, resolvins, and protectins in the prevention and treatment of diabetic macular edema and retinopathy. Nutrition. 2013, 29(1), 1-7.
Xu, H., et al. Para-inflammation in the aging retina. Prog Retin Eye Res. 2009, 28(5), 348-68.
Ryan, A. et al. Lipoxins: regulators of resolution. Curr Opin Pharmacol. 2010,10(2), 166-72.
Tassoni, D., et al. The role of eicosanoids in the brain. Asia Pac J Clin Nutr. 2008, 17 Suppl 1, 220-228.
Tezel, G., et al. TNF-alpha and TNF-alpha receptor-1 in the retina of normal and glaucomatous eyes. Invest Ophthalmol Vis Sci. 2001, 42(8), 1787-1794.
Pascolini, D., et al. 2002 global update of available data on visual impairment: a compilation of population-based prevalence studies Ophthalmic Epidemiol. 2004, 11(2), 67-115.
Romano, M., et al. Activation of human monocytes and the acute monocytic leukemia cell line (THP-1) by lipoxins involves unique signaling pathways for lipoxin A4 versus lipoxin B4: evidence for differential Ca2+ mobilization. Journal of Immunology. 1996, 157(5), 2149-54.
Serhan, C. N., et al. Lipoxins: novel series of biologically active compounds formed from arachidonic acid in human leukocytes. Proc Natl Acad Sci USA. 1984, 81(17), 5335-5339.
Czapski, G. A., et al. The Lipoxygenases: Their Regulation and Implication in Alzheimer's Disease. Neurochem Res. 2016, 41(1-2), 243-257.
Almasieh, M., et al. The molecular basis of retinal ganglion cell death in glaucoma. Prog Retin Eye Res. 2012, 31(2), 152-181.
Liddelow, S.A., et al. Neurotoxic reactive astrocytes are induced by activated microglia. Nature. 2017, 541(7638), 481-7.
Martini, A.C., et al. Neuroprotective effects of lipoxin A4 in central nervous system pathologies. Biomed Res Int. vol. 2014, 2014, ID 316204, 1-9.
Yuan, L., et al. Tumor necrosis factor-alpha: a potentially neurodestructive cytokine produced by glia in the human glaucomatous optic nerve head. Glia. 2000, 32(1), 42-50.
Calandria J.M., et al. NPD1-mediated stereoselective regulation of BIRC3 expression through cREL is decisive for neural cell survival. Cell Death Differ. 2015; 22(8):1363-77.
Livne-Bar, I., et al. Pharmacologic inhibition of reactive gliosis blocks TNF-alpha-mediated neuronal apoptosis. Cell death & disease. 2016, 7(9), e2386,1-12.
Sofroniew, M. V. Astrogliosis. Cold Spring Harbor perspectives in biology. 2014,7(2), 1-16.
Heijl, A., et al. Reduction of intraocular pressure and glaucoma progression: results from the Early Manifest Glaucoma Trial. Archives of ophthalmology. 2002, 120(10), 1268-79.
Exler, R. E., et al. Biomechanical insult switches PEA-15 activity to uncouple its anti-apoptotic function and promote erk mediated tissue remodeling Exp Cell Res 2016, 340(2), 283-94.
Guo, X., et al. PGC-1 alpha Signaling Coordinates Susceptibility to Metabolic and Oxidative Injury in the Inner Retina. Am J Pathol. 2014, vol. 184, No. 4, 1019-1029.
Hernandez, M. R., et al. Astrocytes in glaucomatous optic neuropathy. Prog Brain Res. 2008, 173, 353-73.

Liu, H. H., et al. Chronic ocular hypertension induced by circumlimbal suture in rats. Invest Ophthalmol Vis Sci. 2015, 56(5), 2811-20.
Maddox, J. F., et al. Lipoxin A4 stable analogs are potent mimetics that stimulate human monocytes and THP-1 cells via a G-protein-linked lipoxin A4 receptor. J Biol Chem. 1997, 272(11), 6972-8.
Bazan, N. G. Neuroprotectin D1 (NPD1): a DHA-derived mediator that protects brain and retina against cell injury-induced oxidative stress. Brain Pathol. 2005, 15(2), 159-66.
Maddox, J. F., et al. Lipoxin A4 and B4 are potent stimuli for human monocyte migration and adhesion: selective nactivation by dehydrogenation and reduction. J Exp Med 1996, 183(1), 137-46.
Chiang, N., et al. Identification of resolvin D2 receptor mediating resolution of infections and organ protection. J Exp Med. 2015, 212(8), 1203-17.
O'Sullivan, T. P., et al. Aromatic lipoxin A4 and lipoxin B4 analogues display potent biological activities. J Med Chem. 2007, 50(24), 5894-902.
Livne-Bar, I., et al. Astrocyte-derived lipoxins A4 adn B4 promote neuroprotection from acute and chronic injury. J Clin Invest, 2017, 127(12), 4403-4414.
Bennett, M., et al. Lipid Mediators in Inflammation. Microbiol Spectr. 2016, 4(6), 1-33.
Gordon, W.C., et al. Mediator lipidomics in ophthalmology: targets for modulation in inflammation, neuroprotection and nerve regeneration. Curr Eye Res. 2013, 38(10), 995-1005.
Nahirnyj, A., et al. ROS Detoxification and Proinflammatory Cytokines Are Linked by p38 MAPK Signaling in a Model of Mature Astrocyte Activation. PLoS One 2013, 8(12), e83049, 1-10.
Gronert, K. Resolution, the grail for healthy ocular inflammation. Exp Eye Res. 2010, 91(4), 478-85.
Kwon, Y. H., et al. Primary open-angle glaucoma. The New England journal of medicine. 2009, 360(11), 1113-24.
Wang, X., et al. Resolution of inflammation is altered in Alzheimer's disease. Alzheimers Dement. 2015, 11(1), 40-50 e1-2.
Serhanm C. N., et al. Protectins and maresins: New pro-resolving families of mediators in acute inflammation and resolution bioactive metabolome. Biochimica et biophysica acta. 2015, 1851(4), 397-413.
Serhan, C. N. Novel Pro-resolving lipid mediators are leads for resolution physiology. Nature. 2014, 510(7503), 92-101.
Weinreb, R. N., et al. Primary open-angle glaucoma. Nat Rev Dis Primers. 2016, 2(16067), 1-19.
Tezel, G., et al. Increased production of tumor necrosis factor-alpha by glial cells exposed to simulated ischemia or elevated hydrostatic pressure induces apoptosis in cocultured retinal ganglion cells. J Neurosci. 2000, 20(23), 8693-700.
Pekny, M., et al. Astrocyte reactivity and reactive astrogliosis: costs and benefits. Physiological reviews. 2014, 94(4), 1077-98.
Claria, J., et al. Aspirin triggers previously undescribed bioactive eicosanoids by human endothelial cell-leukocyte nteractions. Proc Natl Acad Sci USA. 1995, 92(21), 9475-9.
Rogers, R. S., et al. Proteomics analyses of human optic nerve head astrocytes following biomechanical strain. Mol Cell Proteomics. 2012, 11(2), M111 012302, 1-17.
Sapieha, P., et al. 5-Lipoxygenase metabolite 4-HDHA is a mediator of the antiangiogenic effect of omega-3 polyunsaturated fatty acids. Sci Transl Med. 2011, 3(69), 69ra12., 1-12.
Sivak, J. M. The aging eye: common degenerative mechanisms between the Alzheimer's brain and retinal disease. Invest Ophthalmol Vis Sci. 2013, 54(1), 871-80.
Tezel, G. The role of glia, mitochondria, and the immune system in glaucoma. Invest Ophthalmol Vis Sci. 2009, 50(3), 1001-12.
Corminboeuf, O., et al. FPR2/ALXR Agonists and the Resolution of Inflammation. Journal of Medicinal Chemistry, Jul. 11, 2014, 1-23.
Dunn, H. C. Restoration of Lipoin A4 Signaling Reduces Alzheimer's Disease-Like Pathology in the 3xTg-AD Mouse Model. J Alzheimers Dis. 2015, 43(3), 893-903.
Wang, Y., et al. Naja sputatrix venom preconditioning attenuates neuroinflammation in a rat model of surgical brain injury via PLA2/5-LOX/LTB4 cascade activation. Scientific Reports. Jul. 2017, 7:5466, 1-12.
Stama, M. L., et al. Novel ureidopropanamide based N-formyl peptide receptor 2 (FPR2) agonists with potential application for

(56) References Cited

OTHER PUBLICATIONS central nervous system disorders characterized by neuroinflammation. European Journal of Medicinal Chemistry, Sep. 2017, 141, 703-720.

Jin, W., et al. Lipoxin A4 methyl ester ameliorates cognitive deficits induced by chronic cerebral hypoperfusion through activating ERK/Nrf? signaling pathway in rats. Pharmacology, Biochemistry and Behavior, 2014, 124, 145-152.

Anderson D. R., et al. Natural history of normal-tension glaucoma. Ophthalmology. 2001;108(2): 247-53.

Biteman B., et al. Interdependence of lipoxin A4 and heme-oxygenase in counter-regulating inflammation during corneal wound healing. FASEB J. 2007; 21(9): 2257-66.

Borgeson E., et al. Lipoxin A4 Attenuates Obesity-Induced Adipose Inflammation and Associated Liver and Kidney Disease. Cell Metab. 2015; 22(1): 125-37.

Calandria J. M., et al. The Docosanoid Neuroprotectin D1 Induces TH-Positive Neuronal Survival in a Cellular Model of Parkinson's Disease. Cell Mol Neurobiol. 2015; 35(8): 1127-36.

Caprioli J. Glaucoma: a disease of early cellular senescence. Invest Ophthalmol Vis Sci. 2013; 54(14):ORSF60-7.

Chen L., et al. Role of the immune modulator programmed cell death-1 during development and apoptosis of mouse retinal ganglion cells. Invest Ophthalmol Vis Sci. 2009; 50(10): 4941-8.

Chung W. S., et al. Do glia drive synaptic and cognitive impairment in disease? Nat Neurosci. 2015; 18(11): 1539-45.

Cohen-Cory S., et al. Effects of brain-derived neurotrophic factor on optic axon branching and remodelling in vivo. Nature. 1995; 378(6553): 192-6.

Doty K. R., et al. The role of the immune system in neurodegenerative disorders: Adaptive or maladaptive? Brain Res. 2015; 1617, 155-73.

Fang X., et al. Human Mesenchymal Stem (Stromal) Cells Promote the Resolution of Acute Lung Injury in Part through Lipoxin A4. Journal of Immunology. 2015; 195(3):875-81.

Fortune B., et al. Selective ganglion cell functional loss in rats with experimental glaucoma. Invest Ophthalmol Vis Sci. 2004; 45(6): 1854-62.

Gomez-Ramos P., et al. Kainic acid prevents peroxidase labeling of retinal ganglion cell bodies in the rat: a possible gate in retrograde axonal transport. Neurosci Lett. 1983; 35(1):1-6.

Ganesh B. S., et al. Inhibition of reactive gliosis attenuates excitotoxicity-mediated death of retinal ganglion cells. PLoS One. 2011; 6(3):e18305, 1-12.

Gregor J. I., et al. Effects of selective COX-2 and 5-LOX inhibition on prostaglandin and leukotriene synthesis in ductal pancreatic cancer in Syrian hamster. Prostaglandins Leukot Essent Fatty Acids. 2005; 73(2):89-97.

Gronert K. Lipid autacoids in inflammation and injury responses: a matter of privilege. Mol Interv. 2008; 8(1):28-35.

Wilson M. R., et al. Intraocular Pressure: Does it Measure Up? Open Ophthalmol J. 2009; 3, 32-7.

Harada C., et al. ASK1 deficiency attenuates neural cell death in GLAST-deficient mice, a model of normal tension glaucoma. Cell Death Differ. 2010; 17(11):1751-9.

Hassan I. R., et al. Acute changes in dietary omega-3 and omega-6 polyunsaturated fatty acids have a pronounced impact on survival following ischemic renal injury and formation of renoprotective docosahexaenoic acid-derived protectin D1. Journal of immunology. 2009; 182(5): 3223-32.

He N., et al. Amyloid-beta(1-42) oligomer accelerates senescence in adult hippocampal neural stem/progenitor cells via formylpeptide receptor 2. Cell death & disease. 2013; 4,e924, 1-10.

Hofer M. M., et al. Brain-derived neurotrophic factor prevents neuronal death in vivo. Nature. 1988; 331(6153):261-2.

Ivanov I., et al. Structural and functional biology of arachidonic acid 15-lipoxygenase-1 (ALOX15). Gene. 2015; 573 (1):1-32.

Johnson T. V., et al. Rodent models of glaucoma. Brain Res Bull. 2010; 81(2-3):349-58.

Josephy-Hernandez S., et al. Neurotrophin receptor agonists and antagonists as therapeutic agents: An evolving paradigm. Neurobiol Dis. 2017; 97(Pt B):139-55.

Klein R. S., et al. Infectious immunity in the central nervous system and brain function. Nat Immunol. 2017; 18 (2):132-41.

Lebrun-Julien F., et al. ProNGF induces TNF-alpha-dependent death of retinal ganglion cells through a p75NTR non-cell-autonomous signaling pathway. Proc Natl Acad Sci USA. 2010; 107(8):3817-22.

Lee Y., et al. Proteomic analysis of glutamate-induced toxicity in HT22 cells. Proteomics. 2007; 7(2):185-93.

Levi-Montalcini R., et al. Destruction of the Sympathetic Ganglia in Mammals by an Antiserum to a Nerve-Growth Protein. Proc Natl Acad Sci USA. 1960; 46(3):384-91.

Liu H. H., et al. Reversal of functional loss in a rat model of chronic intraocular pressure elevation. Ophthalmic Physiol Opt. 2017; 37(1):71-81.

Liu H. H., et al. A Mouse Model of Chronic Ocular Hypertension Induced by Circumlimbal Suture. Invest Ophthalmol Vis Sci. 2017; 58(1):353-61.

Mariga A., et al. Consequences of brain-derived neurotrophic factor withdrawal in CNS neurons and implications in disease. Neurobiol Dis. 2017; 97(Pt B):73-9.

Mukherjee P. K., et al. Neuroprotectin D1: a docosahexaenoic acid-derived docosatriene protects human retinal pigment epithelial cells from oxidative stress. Proc Natl Acad Sci USA. 2004; 101(22):8491-6.

Nishijima K., et al. Vascular endothelial growth factor-A is a survival factor for retinal neurons and a critical neuroprotectant during the adaptive response to ischemic injury. Am J Pathol. 2007; 171(1):53-67.

Oppenheim R. W., et al. Naturally occurring and induced neuronal death in the chick embryo in vivo requires protein and RNA synthesis: evidence for the role of cell death genes. Dev Biol. 1990; 138(1):104-13.

Parkinson J. F. Lipoxin and synthetic lipoxin analogs: an overview of anti-inflammatory functions and new concepts in mmunomodulation. Inflamm Allergy Drug Targets. 2006;5(2):91-106.

Parpura V., et al. Glial cells in (patho)physiology. J Neurochem. 2012;121(1):4-27.

Quigley H. A.. New paradigms in the mechanisms and management of glaucoma. Eye. 2005;19(12):1241-8.

Reichardt L. F.. Neurotrophin-regulated signalling pathways. Philos Trans R Soc Lond B Biol Sci. 2006;361 (1473):1545-64.

Riesenberg A. N., et al. Rbpj cell autonomous regulation of retinal ganglion cell and cone photoreceptor fates in the mouse retina. J Neurosci. 2009;29(41):12865-77.

Serhan C. N., et al. Mediator lipidomics: search algorithms for eicosanoids, resolvins, and protectins. Methods in enzymology. 2007;432, 275-317.

Smith H. K., et al. Targeting formyl peptide receptor 2 reduces leukocyte-endothelial interactions in a murine model of stroke. FASEB J. 2015;29(5):2161-71.

Stanciu M., et al. Persistent activation of ERK contributes to glutamate-induced oxidative toxicity in a neuronal cell line and primary cortical neuron cultures. J Biol Chem. 2000;275(16):12200-6.

Wang Q., et al. Kainic acid-mediated excitotoxicity as a model for neurodegeneration. Mol Neurobiol. 2005;31 (1-3):3-16.

International Patent Application No. PCT/CA2018/050288, International Search Report, dated Jun. 7, 2018, 5 pages.

International Patent Application No. PCT/CA2018/050288, Written Opinion of the International Searching Authority, dated Jun. 7, 2018, 7 pages.

* cited by examiner

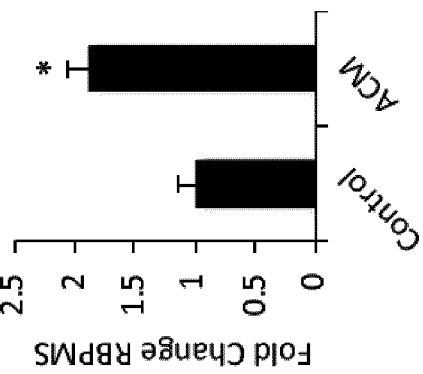
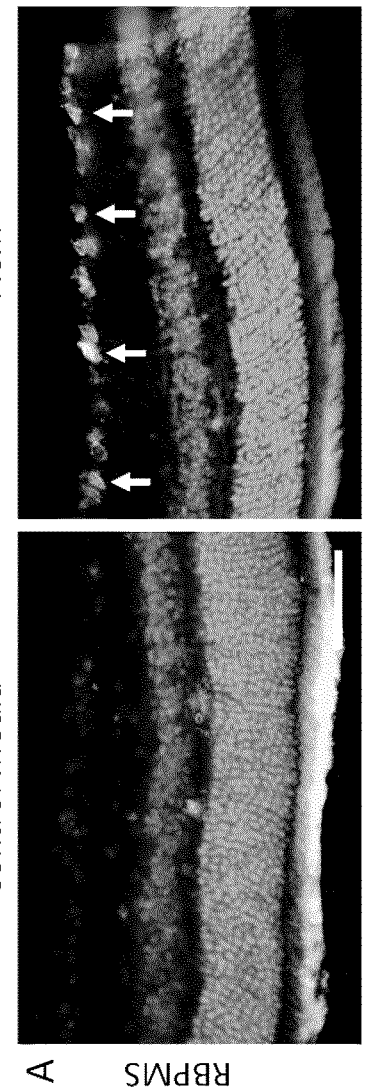
Fig. 2A
Fig. 2B
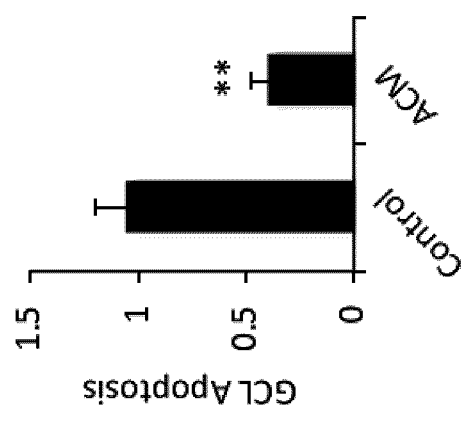
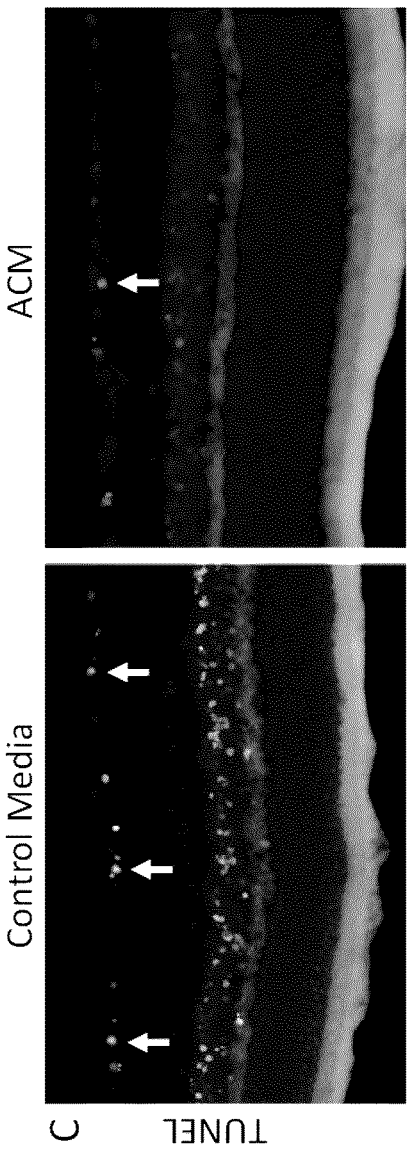
Fig. 2C
Fig. 2D

Fig. 2E
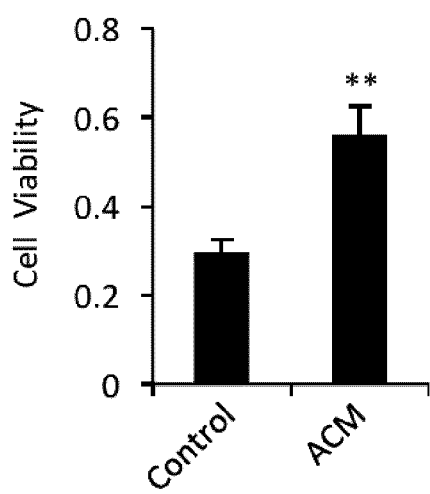
Fig. 2F
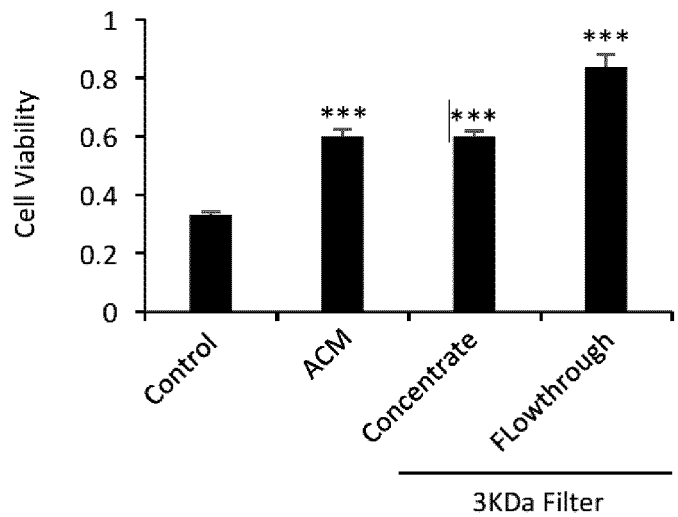
Fig. 2G
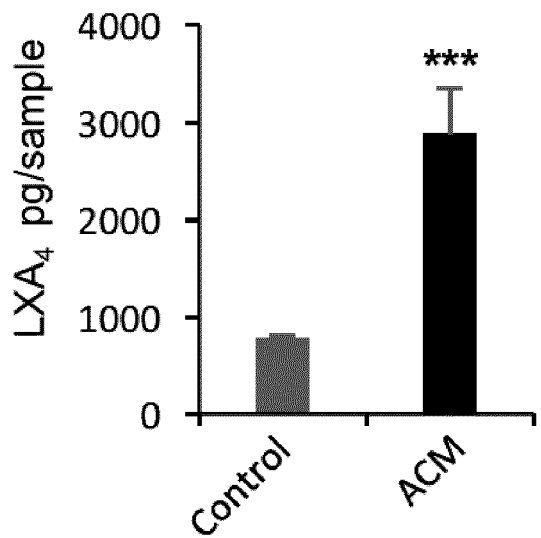
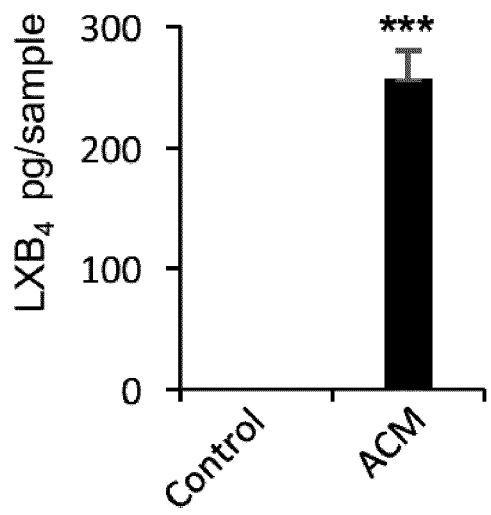

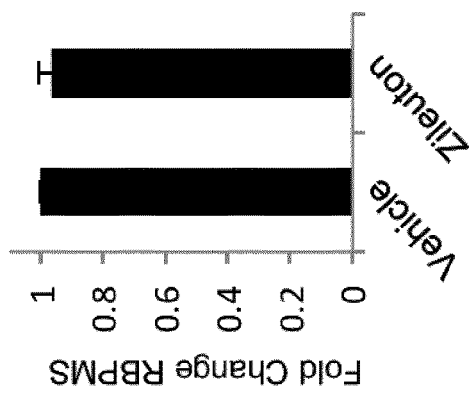
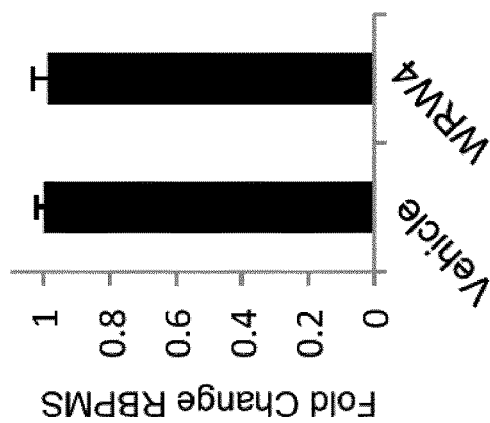
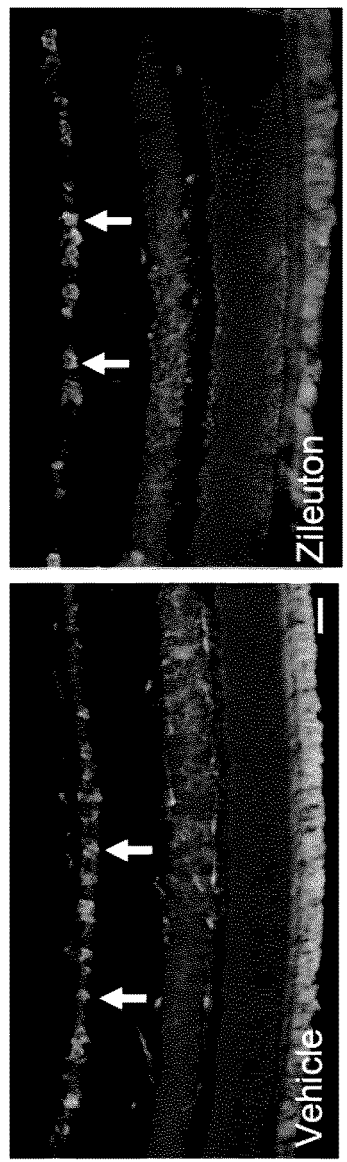
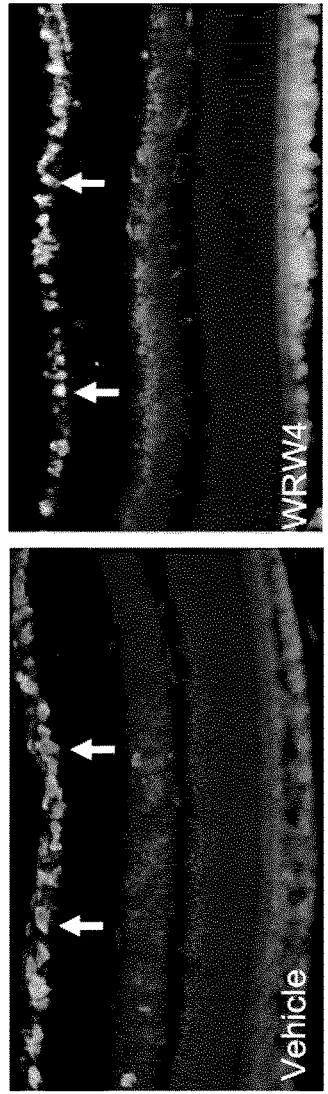

LIPOXIN AND LIPOXIN ANALOGUE MEDIATED NEUROPROTECTION AND TREATMENTS

CROSS REFERENCE TO RELATED APPLICATION

This is a Patent Cooperation Treaty Application which claims the benefit of 35 U.S.C. § 119 based on the priority of U.S. Provisional Patent Application No. 62/469,396, filed Mar. 9, 2017 which is incorporated herein by reference in its entirety.

This invention was made with government support under grant EY026082 awarded by the NIH. The government has certain rights in the invention.

FIELD

The disclosure relates to methods and uses of lipoxins, lipoxin analogues and 5-LO activating agents for neuroprotection, and particularly for treating neural disorders and conditions and in particularly retinal ganglion cell neuron related disorders and diseases.

BACKGROUND

Neurodegeneration in response to stress or injury has been associated with both the induction of neuroinflammatory signals (1-4), and a corresponding loss of homeostatic prosurvival cues (5-8). However, the mechanisms by which these activities are coordinated in the central nervous system (CNS) remain unclear. The vulnerable inner retina provides an accessible model for studying CNS injury (9, 10), where progressive damage is a hallmark of the common and incurable neurodegenerative disease glaucoma (11-13). In this neurovascular tissue, highly active retinal ganglion cell neurons (RGCs) interact intimately with neighboring astrocytes, Müller glia, and vascular endothelia (14, 15).

Lipoxins are autacoids; specialized pro-resolving lipid mediators (SPMs) that act locally in paracrine or autocrine manners and are rapidly metabolized. They belong to an increasingly complex family of small polyunsaturated fatty acid (PUFA)-derived enzymatic products, which direct potent cellular responses to dampen inflammation, resolve inflammatory PMN and restore cellular homeostasis (16-18). PUFAs derived from docosahexaenoic acid (DHA) have been investigated for roles in neuroinflammation, including resolvins, maresins, and protectins (19, 20). In particular, neuroprotection D1 (NPD1) has established antiapoptotic and neuroprotective actions following oxidative stress or injury in the brain and retina in addition to pro-resolving functions (21-23). In contrast the role of lipoxins in neuroprotection has not been explored. Lipoxins were the first identified SPMs, and are formed by sequential oxygenation via the conserved lipoxygenase enzymes, 5-LOX and 12/15-LOX. These eicosanoids are derived from arachidonic acid (AA), and are structurally distinct from DHA-derived NPD1, acting through different receptors (24-26).

There are two endogenous lipoxins, $LXA_4$, and $LXB_4$, which display a wide range of anti-inflammatory and pro-resolving activities. $LXA_4$ is by far the more well studied, binds GPR32 in humans, and also binds with high affinity to the GPCR Formyl Peptide Receptor 2 (FPR2, ALX) to mediate effects in a variety of immune cells, vascular endothelia, and microglia. These effects include activities in leukocyte recruitment, angiogenesis, and inhibition of NFκB mediated release of IL-6 and TNF-α (24, 25, 27). In comparison, although $LXB_4$ has some overlapping bioactivity, its mechanism of action and signaling pathway are distinct from $LXA_4$ (28). $LXB_4$ has potent action with macrophages and triggers non-phlogistic activation of human monocytes in the picomolar range. Despite its potent bioactions no receptor for $LXB_4$ has been established (24, 25). Consequently, $LXB_4$ has been less studied than $LXA_4$, with little known about its functions in the CNS or roles in neurodegeneration. Loss of $LXA_4$ and/or lipoxygenase activities have been investigated to define their neuroinflammatory roles in Alzheimer's disease (AD), stroke, and neuropathic pain (29-32). In the eye, $LXA_4$ and related SPMs have roles in corneal wound healing, uveitis, autoimmune dry eye disease, and diabetic retinopathy (19, 33-36). However, a direct role for lipoxin signaling on neuronal homeostasis and survival has not been identified.

SUMMARY

Methods and compositions for inhibiting or preventing neurodegeneration, specifically hippocampal or optic nerve or retinal ganglion cell neuron (RGC) degeneration and/or cell loss comprising administering to a subject an effective amount of one or more lipoxin compounds and/or lipoxin analogues such that degeneration and/or cell loss of RGCs is inhibited or prevented.

An aspect of the disclosure includes a method for providing neuroprotection, optionally retinal neuroprotection, and/or treating a neural disorder or condition comprising administering to a subject in need thereof an effective amount of one or more lipoxin compounds and/or lipoxin analogues.

Another aspect of the disclosure includes a composition comprising one or more lipoxin compounds and/or lipoxin analogues, each or in combination, at a concentration of at least 0.2 nM and optionally less than 1 mM, optionally wherein the composition is in a dosage form and the dosage form comprises between 1 ng and 10 micrograms of the one or more lipoxin compounds and/or lipoxin analogues.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 1A to FIG. 1N are a series of images and FIG. 1O to FIG. 1P are graphs showing transplanted retinal astrocytes protect inner retinal neurons in vivo. FIG. 1A shows control eyes injected with PBS showed typical neuronal staining with Islet1 (arrows) in the GCL and INL. FIG. 1B shows that challenge with KA led to rapid loss of signal (bar indicates 50 μm). FIG. 1C shows that Islet1 staining was strongly rescued by transplantation of RA's. (FIG. 1K-FIG. 1N) are corresponding images of TUNEL staining that showed higher GCL or INL apoptosis in the controls compared to RA transplants. FIG. 1O is a graph showing quantification of Islet1 results for each group (FIG. 1A-FIG. 1C, FIG. 1G-FIG. 1J), showing significant protection of GCL neurons by RAs that is absent in each of the controls (**$p<0.01$ compared to PBS, n=10 animals, bars are S.E.M.). FIG. 1P shows quantification of TUNEL results for each group (FIG. 1D-FIG. 1F, FIG. 1K-FIG. 1N), showing a significant reduction of apoptosis by RAs that is lower or absent in the controls (*$p<0.05$, ***$p<0.005$, n=10 animals, bars are S.E.M.).

FIG. 2A and FIG. 2C are series of images and FIG. 2B and FIG. 2D to FIG. 2G are graphs showing astrocyte neuroprotection is mediated by a secreted activity that is enriched in lipoxins. FIG. 2A shows results with astrocyte conditioned media (ACM) or cell free control media that was injected intravitreally, one day prior to KA challenge. ACM treatment strongly rescued KA induced RGC loss compared to cell free control media, as detected by RBPMS signal (arrows) (bar indicates 50 μm). FIG. 2B shows quantification of the RBPMS results in FIG. 2A showing significant ACM protection (*$p<0.05$, n=5 animals, bars represent S.E.M.). FIG. 2C shows complimentary results showing ACM mediated reduction in TUNEL labelled apoptotic cells (arrows) compared to control media. FIG. 2D shows quantification of TUNEL results in FIG. 2C showing significant decrease in GCL apoptosis by ACM media (**$p<0.01$, n=5 animals, bars are S.E.M.).

FIG. 2E demonstrates that the protective effect of ACM was reproduced in vitro with HT22 cells challenged with 5 mM glutamate (**$p<0.01$, n=3, bars are S.E.M.). FIG. 2F demonstrates that a substantial protective activity in ACM is contained in a 3 kDa filtrate. (*$p<0.005$, n=3, bars are S.E.M.). FIG. 2G shows high concentrations of the lipoxins, $LXA_4$ and $LXB_4$, were detected in ACM compared to control media by LC-MS/MS (Scale bar indicates 50 μm, *$p<0.05$, $p<0.01$, *$p<0.005$, bars are S.E.M.).

FIG. 3A is a graph of qRT-PCR of mouse retinal cDNA that shows there is a significantly reduced expression Alox5, and Fpr2, but not Alox15, two hours after KA insult compared to PBS controls, (*$p<0.005$, n=3, bars are S.E.M.). FIG. 3B is a graph showing $LXB_4$ concentrations in total mouse retina are reduced at 6 hrs following injury, while $LXA_4$ concentrations are reduced in the ON (optic nerve) compared to PBS injected controls (n=10 retinas/aggregate group). FIG. 3C is a series of confocal microscopy images that shows strong 5-LOX immunostaining is present in primary retinal astrocytes (bar=20 μm). FIG. 3D is a series of confocal imaging of 5-LOX immunostaining that shows accumulation in the GCL and NFL, with partial colocalization (arrows) with astrocytes (GFAP; bar=10 μm). FIG. 3E is a series of images that shows that signal for 5-LOX in the inner retina is reduced at three and six hours after injury (arrow). FIG. 3F is a series of images that shows that FPR2 immunostaining is prominent in cultured primary RGCs and colocalizes with β3-tubulin (bar=20 μm). FIG. 3G is a series of images that shows that ALX/FPR2 immunostaining is specific to the GCL and co-localizes (arrows) with the RGCs (RGC marker Brn3a) (Scale bars indicate 20 μm (C, F) or 10 μm (D, G), *$p<0.005$, bars are S.E.M).

FIG. 4A is a series of images showing that intravitreal injection of 10 μM $LXA_4$ or $LXB_4$ prior to KA-induced insult resulted in increased RGC survival compared to vehicle control (PBS), as shown by RBPMS staining (arrows). FIG. 4B is a graph of the corresponding quantification and shows significant increases in RGC survival with $LXA_4$ or $LXB_4$ treatment compared to vehicle control. Values are presented as fold change from non-injured controls (*$p<0.05$ compared to PBS+KA, n=8; bars are S.E.M.). FIG. 4C is a series of images and FIG. 4D is a corresponding graph that shows intravitreal treatment with 10 μM of the 5-LOX inhibitor, Zileuton, significantly compromised RGC survival following acute stress compared to vehicle (*$p<0.05$, n=5, bars are SE). FIG. 4E-FIG. 4F which are a series of images and a corresponding graph respectively, show that 15 μM of the ALX/FPR2 inhibitor, WRW4, significantly reduced RGC survival following acute stress compared to vehicle (Scale bar indicates 50 μm, *$p<0.05$, n=5, bars are S.E.M.).

FIG. 5A is a graph showing that treatment of HT22 neuronal cells with $LXA_4$ or $LXB_4$ significantly protected them from metabolic insult in a dose dependent manner up to 500 nM (n=3). FIG. 5B is a graph that shows that no protective activity was observed by treatment with up to 1 μM of the related molecules 15-HETE or RvD2 (n=3). FIG. 5C is a graph that shows that $LXB_4$ protective activity at 500 nM was not blocked by treatment with increasing μM concentrations of WRW4, or the GPR18 antagonist O-1918 (n=3, bars are S.E.M.).

FIG. 5D is a graph showing Mitotracker red signal which indicates protection from increased membrane potential with $LXB_4$ treatment (n=3). FIG. 5E is a series of images showing primary RGCs labeled with β3-tubulin extend an extensive network of neurites that disintegrate dramatically after 24 hours of 30 μM PQ. Intact neurites are significantly maintained by 1 μM $LXB_4$, but not $LXA_4$ or RvD2. FIG. 5F is a graph that shows RGC survival following oxidative stress demonstrates significant rescue with treatment by $LXA_4$ or $LXB_4$ (n=3). FIG. 5G is a graph that shows RGC neurite degeneration following PQ challenge was significantly rescued by $LXB_4$, but not $LXA_4$ or RvD2 (n=3). FIG. 5H is a graph showing that primary cortical neurons demonstrate a similar protective effect for $LXB_4$ (n=5). (Scale bar indicates 20 μm, *$p<0.05$, **$p<0.01$, bars are S.E.M.). FIG. 5I is a series of images of primary RGCs labeled with β3-tubulin and shows they extend an extensive network of neurites. RGC and neurite number are dramatically reduced after 48 hours of serum deprivation (SD), but are rescued by treatment with 1 μM $LXA_4$ or $LXB_4$ (bar indicates 40 μm). FIG. 5J is a graph showing quantification of neuron survival following SD and demonstrates significant rescue with treatment by $LXA_4$ or $LXB_4$ (*$p<0.05$, **$p<0.01$, n=3, bars are S.E.M.). FIG. 5K is a series of images showing that neurite degeneration following SD was strongly rescued by $LXB_4$, but not $LXA_4$ (bar indicates 40 μm). FIG. 5L Quantification of intact neurite extensions shows significant rescue by $LXB_4$ (*$p<0.05$, n=3, bars are S.E.M.).

FIG. 6 is a series of graphs showing that therapeutic administration of $LXB_4$ protects RGC function following chronic IOP injury.

FIG. 7A is a series of images showing representative retinal BRN3a stained flatmounts after 15 weeks of elevated IOP (sutured) compared to contralateral control eyes, from LXB$_4$ treated or vehicle. FIG. 7B is a graph showing quantification of RGC density which revealed the suture induced loss was significantly rescued by LXB$_4$ treatment compared to vehicle in both the outer and inner retinas (***p<0.001 compared to vehicle, n=8, bars are S.E.M.).

FIG. 8A is an image showing that primary retinal astrocytes express GFAP. FIG. 8B is an image showing that primary retinal astrocytes express GS, FIG. 8C is an image showing that primary retinal astrocytes express vimentin, and FIG. 8D is an image showing that primary retinal astrocytes express Pax-2 (bar indicates 50 μm). FIG. 8E is a series of blots showing protein extracts from the primary astrocytes grown in control media (Con) or challenged with ROS through exposure to 300 μM PQ, showing increased GFAP, reduced GS, and increased phosphorylation of p38 MAPK (P-p38) compared to total p38 (Pan p38).

FIG. 9A-FIG. 9C are images showing GFAP staining of retinas 16 days after injection with PBS FIG. 9A, or RA FIG. 9B-FIG. 9C. Endogenous activation was not induced at sites directly underlying the injected cells (FIG. 9B, arrow), or distant from them FIG. 9C. FIG. 9D is an image showing tht Ad-GFP transduced RA do not integrate into the recipient retina and remain alive after two weeks (arrow). FIG. 9E-FIG. 9F are images showing there was no TUNEL signal, indicating apoptosis, in transplant retinas FIG. 9E compared to PBS control FIG. 9F, and FIG. 9G-1 are images showing there was no widespread evidence of microglial activation with CD68 (FIG. 9G, neutrophils with GR-1 (FIG. 9H), or macrophage infiltration with F4/80 (FIG. 9I, arrow). (Bar indicates 50 μm).

FIG. 10A-FIG. 10D are images and graphs that show that: lipoxin signaling antagonists had no effect on naïve retinas. Uninjured eyes were injected with either Zileuton (FIG. 10A-FIG. 10B) or WRW4 (FIG. 10C-FIG. 10D), and assessed for RGC loss by staining and counting for RBPMS positive cells. There was no change for either drug (n=5, bars are S.E., scale bar represents 50 μm).

DETAILED DESCRIPTION OF THE DISCLOSURE

I. Definitions

Figures 1A, 1B, 1C:
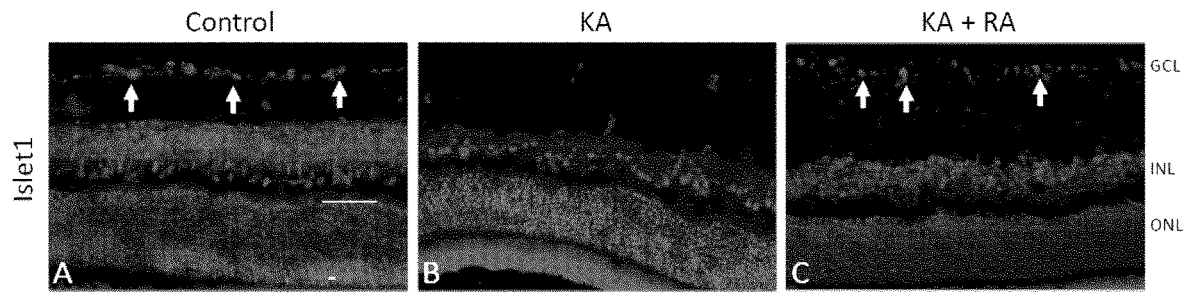

As used herein, the phrase "effective amount" or "therapeutically effective amount" means an amount effective, at dosages and for periods of time necessary to achieve the desired result. For example in the context or treating glaucoma, an effective amount is an amount that for example reduces IOP compared to the response obtained without administration of the compound(s). Effective amounts may vary according to factors such as the disease state, age, sex, weight of the subject. The amount of a given compound that will correspond to such an amount will vary depending upon various factors, such as the given drug or compound, the pharmaceutical formulation, the route of administration, the type of disease or disorder, the identity of the subject or host being treated, and the like.

The phrase "lipoxin compound" as used herein includes naturally occurring lipoxins, including astrocyte secreted lipoxins, Lipoxin A$_4$ (LXA$_4$) compound having the formula 5S,6R,15S-trihydroxy-7E,9E,11Z,13E-eicosatetraenoic acid, Lipoxin B$_4$ (LXB$_4$) compound having the formula 5S,14R,15S-trihydroxy-6E,8Z,10E,12E-eicosatetraenoic acid and epi-lipoxin compounds including but not limited to aspirin induced forms 15-epi-LXA$_4$ (5S,6R,15R-trihydroxy-7E,9E,11Z,13E-eicosatetraenoic acid), and 15-epi-LXB$_4$ (5S,14R,15R-trihydroxy-6E,8Z,10E,12E-eicosatrienoic acid), as well as combinations thereof as well as pharmaceutically acceptable salts and solubilized forms of any of the foregoing. Lipoxins can be synthesized using methods known in the art including as reported in Webber S E, Veale C A, Nicolaou K C (1988) *Adv Exp Med Biol* 229:61 and in *Lipoxins: Biosynthesis, Chemistry, and Biological Activities*, ed P Wong C Serhan, Springer Science+Business Media LLC. They can also be purchased or isolated for example from ACM. For example, $LXB_4$ can be purchased for example from Cayman Chemical and $LXA_4$ can be purchased from Sigma Aldrich.

The term "$LXA_4$" as used herein means

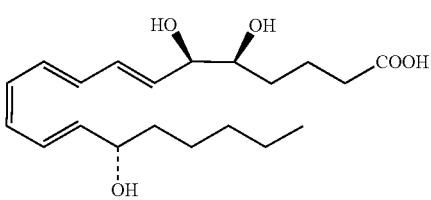 [SMILES: CCCCC[C@H](O)/C=C/C=C\C=C\C=C\[C@@H](O)[C@@H](O)CCCC(=O)O]

or a pharmaceutically acceptable salt thereof.

The term $LXB_4$" as used herein means

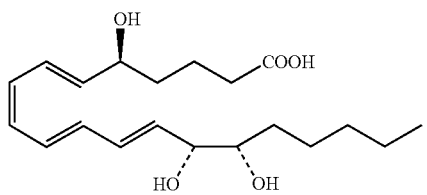 [SMILES: CCCCC[C@H](O)[C@H](O)/C=C/C=C/C=C\C=C\[C@@H](O)CCCC(=O)O]

or a pharmaceutically acceptable salt thereof.

The term "lipoxin analogues" as used herein includes stabilized lipoxin compounds including stabilized epi-lipoxin compounds for example, compounds described in U.S. Pat. Nos. 4,560,514, 5,441,951, 5,648,512, 5,650,435, 6,048,897, 6,627,658, 6,670,396, 8,722,654, 7,741,369 and 7,700,650, as well as analogues described in references 81 and 82 cited herein, each of which are herein incorporated by reference. Especially preferred are, lipoxin analogues having a trihydroxy tetraene or a double bond motif or both that is similar or identical to $LXA_4$ or $LXB_4$ Benzo-lipoxins which are lipoxin analogues that are thermally and metabolically more stable than endogenous lipoxins ($LXA_4$ and $LXB_4$) are examples of lipoxin analogues that can be used. Replacement of the tetraene unit of $LXA_4$ with a benzo-fused ring also allows for efficient synthesis of these analogues. An example of a member of a benzo-lipoxin is 9,12-LXA4. Also included are LXA4 and LXB4 methyl esters.

The lipoxin analogue can be referred to as a $LXA_4$ analogue or a $LXB_4$ analogue, e.g. analogues that are based on the structure of $LXA_4$ or $LXB_4$. For example, distinct $LXA_4$ and LXB4 analogues including metabolically stable analogues are known in the art. Their design is based on inhibiting the dehydrogenation of the hydroxyl group at carbon 15 for $LXA_4$ or the hydroxyl group at carbon 5 for $LXB_4$ to increase the half life in vivo. Any $LXA_4$ and $LXB_4$ analogues that exhibit decreased metabolism by 15-prostaglandin dehydrogenase/eicosanoid oxidoreductase are included herein. An exemplary $LXA_4$ analogue is 5(S),6(R)-7-trihydroxymethyl heptanoate (BML-111) $LXA_4$ analogue. Synthesis schemes for analogues of $LXA_4$ are provided for example in *Heteroaromatic Lipoxin A4 Analogues Synthesis and Biological Evaluation* (2012) Chapter 2, *Recent Advances in the Chemistry and Biology of Stable Synthetic Lipoxin Analogues*. Preferred LXB4 analogues can include analogues wherein the 5-hydroxyl group (or substituted versions thereof) is maintained or where the three hydroxyl groups (or substituted versions thereof) and particularly the relative positions thereof and the tetraene double bond motif are maintained. Also included are compounds that bind and activate the $LXA_4$ receptor FPR2, referred to for example as FPR2 agonists. These include compounds such as Quinc-1 and Mmk-1 (Tocris) as well as FPR2 agonists described in Corminboeuf and Leroy, FPR2/ALXR Agonists and the Resolution of Inflammation. J. Med. Chem., 2015, 58(2):537-59, PMID: 25365541 which is hereby incorporated by reference in its entirety.

As used herein, the term "diluent" refers to a pharmaceutically acceptable carrier which does not inhibit a physiological activity or property of an active compound, such as lipoxin or a lipoxin analogue, to be administered and does not irritate the subject and does not abrogate the biological activity and properties of the administered compound. Diluents include any and all solvents, dispersion media, coatings, surfactants, antioxidants, preservative salts, preservatives, binders, excipients, disintegration agents, lubricants, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The term "neural disorder or condition" includes any and all disorders and conditions that affect the eye and the central nervous system that involve neural degeneration and/or neural cell loss including but not limited to neural injuries associated with hippocampal or RGC degeneration, acute retinal, brain injury, such as angle closure glaucoma, retinal vein occlusions, macular edema, ischemic and hemorrhagic stroke, and traumatic brain injury as well as chronic neurodegenerative retinal or brain disorders such as glaucoma including all forms of primary open angle glaucoma, normal tension glaucoma, as well as retinal ischemias, diabetic retinopathy and diabetic macular edema, age related macular degeneration, retinitis pigmentosa, and Alzheimer's disease (retinal pathology), multiple sclerosis, as well as neurodegenerative brain diseases, such as Alzheimer's disease, Parkinson's disease and ALS.

The term "neuroprotection" as used herein means making a neuron more resistant to a stressor or injury and includes for example inhibiting degeneration, including neurite degeneration and/or further degeneration, promoting survival and/or inhibiting neural cell loss compared to the stressor or injury in the absence of the factor. For example, neurons that are provided one or more lipoxins and/or lipoxin analogues are more resistant to stress compared to similarly treated neurons not administered the one or more lipoxins or lipoxin analogues. Neuroprotection may be desired when a subject is at risk of a neurodegenerative disease and under neural stress and includes prophylactic use for example use with subjects with ocular hypertension (risk for glaucoma), diabetes (risk for diabetic retinopathy, macular edema), or subjects with drusen or age related macular degeneration (exudative or non-exudative forms), as well as for example subjects with a family history of dementia, Alzheimer's disease, Parkinson's disease, etc. Neuroprotection may be desired also after an injury or disease that affects neurons, to protect for example neighbouring neurons from degeneration including neurite degeneration.

The term "central nervous system neurodegeneration and/or neural cell loss" as used herein includes for example degeneration and/or loss of any neurons of the central nervous system including hippocampal neurons, optic neurons and/or retinal ganglion cell (RGC) neurons. Further, the phrase "inhibiting central nervous system neurodegeneration and/or neural cell loss" in the context of administering one or more compounds described herein, means decreasing the number of neurons affected by at least 10%, at least 20%, at least 30%, at least 40% or more compared to the number of neurons affected under similar conditions in the absence of administering the compound.

The term "subject" as used herein includes all members of the animal kingdom including mammals, and suitably refers to humans.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. Treatment methods comprise administering to a subject a therapeutically effective amount of one or more compounds described in the application and optionally consists of a single administration, or alternatively comprises a series of applications. For example, the compounds described herein may be administered at least once a week, about one time per week to about once daily for a given treatment or the compound may be administered one, two, three or four times daily, for example twice daily. The length of the treatment period depends on a variety of factors, such as the severity of the disease, the age of the patient, the concentration, the activity of the compounds described herein, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

In the specification and in the claims, the terms "including" and "comprising" are open-ended terms and should be interpreted to mean "including, but not limited to". These terms encompass the more restrictive terms "consisting essentially of" and "consisting of". It is also to be noted that the terms "comprising", "including", "characterized by" and "having" can be used interchangeably.

As used herein and in the appended claims, the singular forms "a", "an", and "the" include plural reference unless the context clearly dictates otherwise. As well, the terms "a" (or "an"), "one or more" and "at least one" can be used interchangeably herein.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Unless defined otherwise, all technical and scientific terms used herein have the same meanings as commonly understood by one of ordinary skill in the art.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods and Compositions

It is demonstrated herein that resting astrocytes from the inner retina secrete neuroprotective lipoxin molecules, $LXA_4$ and $LXB_4$. Using the hippocampal cell line HT22 it is demonstrated that treatment with astrocyte secretions containing lipoxins produced significant HT22 cell protection from glutamate induced cell death as shown in FIG. 2E. Like $LXA_4$, agonists to the $LXA_4$ receptor, reduce mitochondrial oxidative stress. Further it is demonstrated that either $LXA_4$ or $LXB_4$ are sufficient to directly promote primary retinal ganglion cell neuron (RGC) neuroprotection in vitro, and in vivo in acute and chronic retinal disease models. Still further it is demonstrated that the optic nerve also releases $LXA_4$ when not under stress but that this activity is substantially reduced under stress. Finally, lipoxins were also shown to provide neuroprotection in primary cortical neurons and a dopaminergic neural cell line suggesting that lipoxins can be useful for preventing neuron loss and treating neurodegenerative diseases such as Alzheimer's disease and Parkinson's disease.

Accordingly an aspect includes a method of providing neuroprotection comprising administering to a subject in need thereof an effective amount of one or more lipoxin compounds and/or lipoxin analogues.

In an embodiment, the neuroprotection is for central nervous system neuroprotection, optionally hippocampal neuroprotection or cortical neuron protection. In another embodiment, the neuroprotection is retinal neuroprotection, optic nerve neuroprotection or RGC neuroprotection.

The neuroprotection can be provided to inhibit neurodegeneration including neurite degeneration and/or to prevent neural cell loss. A subject at risk of developing a disease or condition affecting the central nervous system, retinal neurons, optic nerve or RGC may be a suitable candidate for receiving an effective amount of one or more lipoxin compounds and/or lipoxin analogues.

In an embodiment, the subject has sustained an ischemic and hemorrhagic stroke, or a brain injury such as a traumatic brain injury.

In an embodiment, the lipoxin and/or lipoxin analogue is administered to a subject with ocular hypertension (risk for glaucoma), diabetes (risk for diabetic retinopathy, macular edema), or subjects with drusen or age related macular degeneration (exudative or non-exudative forms). In another embodiment, the lipoxin and/or lipoxin analogue is administered to a subject with a family history of dementia, Alzheimer's disease, Parkinson's disease, etc.

It is also demonstrated that transplants of retinal astrocytes, injection of astrocyte secretions containing lipoxins, and synthetic administration of $LXA_4$ or $LXB_4$ strongly protected neurons in the ganglion cell layer from acute injury induced loss suggesting that $LXA_4$ and $LXB_4$, provide neuroprotective support to RGC that may be compromised following stress or injury.

In a further embodiment, the method is for inhibiting or preventing RGC degeneration and/or cell loss, optionally resulting from acute injury, the method comprising administering to a subject in need thereof an effective amount of one or more lipoxin compounds and/or lipoxin analogues such that degeneration and/or cell loss of RGCs is inhibited or prevented.

In an embodiment, the method is for treating vision loss, occurring for example related to an acute injury and/or chronic condition.

In an embodiment, the subject is afflicted with an acute retinal injury, such as angle closure glaucoma, retinal vein occlusions, or macular edema.

It was further demonstrated, that lipoxins, and $LXB_4$ in particular, are therapeutically effective for treating neural disorders such as chronic retinal neural disorders. As shown in the Examples using an in vivo rat glaucoma model, there was a significant rescue of RGC function and survival in inner and outer retinas in $LXB_4$ treated eyes compared to vehicle.

In an embodiment, the subject is afflicted with a chronic retinal disorder such as glaucoma.

Another aspect includes a method of treating a neural disorder or condition, the method comprising administering to a subject in need thereof an effective amount of one or more lipoxin compounds and/or lipoxin analogues.

In an embodiment, the neural disorder or condition is a brain disorder, a retinal neural disorder or retinal neural injury associated with RGC degeneration and/or cell loss. In an embodiment, the neural disorder or condition is a chronic neurodegenerative retinal disorder.

In an embodiment, the chronic neurodegenerative retinal or brain disorder comprises, all forms of primary open angle glaucoma, normal tension glaucoma, retinal ischemias, diabetic retinopathy and macular edema, age related macular degeneration, retinitis pigmentosa, multiple sclerosis, and Alzheimer's disease (retinal pathology), as well as neurodegenerative brain diseases, such as Alzheimer's disease and Parkinson's disease.

In an embodiment, the one or more lipoxin compounds is selected from $LXA_4$ (5S,6R,15S-trihydroxy-7E,9E,11Z,13E-eicosatetraenoic acid), $LXB_4$ (5S,14R,15S-trihydroxy-6E,8Z,10E,12E-eicosatetraenoic acid), 15-epi-$LXA_4$ (5S,6R,15R-trihydroxy-7E,9E,11Z,13E-eicosatetraenoic acid) and 15-epi-$LXB_4$ (5S,14R,15R-trihydroxy-6E,8Z,10E,12E-eicosatrienoic acid).

In an embodiment, the one or more lipoxin compounds are or include $LXA_4$ and/or $LXB_4$.

In an embodiment, at least one $LXA_4$ compound or $LXA_4$ analogue and at least one $LXB_4$ compound or $LXB_4$ analogue is administered.

In an embodiment, the one or more lipoxin compounds is or includes $LXA_4$.

In another embodiment, the one or more lipoxin compounds is or includes $LXB_4$.

In an embodiment, one or more lipoxin analogues is/are administered.

In an embodiment the one or more lipoxin analogues is selected from $LXA_4$ and $LXB_4$ analogues disclosed in U.S. Pat. Nos. 6,627,658; 6,635,776; 6,653,493; 6,750,360; 6,887,901; 7,288,569; 7,294,728; 7,770,650; 7,741,369; 7,759,395; 7,803,557; 7,812,054; 7,825,271; 7,872,152; 7,994,219; 8,008,282; 8,093,417; 8,119,691; 8,273,792; 8,569,542; 8,604,229; 8,722,654; 8,933,270; 9,364,454; and 9,463,177, each of which are herein incorporated by reference.

Lipoxins can be purchased for example from Cayman Chemical or Sigma Aldrich, isolated and/or prepared using methods known in the art. Methods for producing or sources of lipoxin analogues include for example methods and sources described in U.S. Pat. Nos. 4,560,514, 5,441,951, 5,648,512, 5,650,435, 6,048,897, 6,627,658, 6,670,396, 8,722,654, 7,741,369 and/or 7,700,650, as well as methods or sources described in references 81 and 82 cited herein, each of which are herein incorporated by reference.

In an embodiment, the lipoxin analogue is a FPR2 agonist. As shown here in FIG. 19, FRR2 agonists, Quin C1 and MmK1. FPR2 agonists are known in the art, including agonists described, and reviewed in Corminboeuf and Leroy, J Med Chem, 2014, 58; 537-559, herein incorporated by reference. Any FPR2 agonist can be used that is for example at least as active as LXA4. Many FPR2 agonists exhibit increased activity compared to LXA4.

The lipoxin compound and/or lipoxin analogue can for example be provided as an ethanol solution, or in aqueous buffers such as phosphate buffered saline.

In an embodiment, a composition comprising one or more lipoxin compounds and/or lipoxin analogues is administered.

In another aspect, the disclosure provides a method for providing neuroprotection, optionally retinal neuroprotection, and/or treating or preventing a neural disorder or condition comprising administering to a subject in need thereof an effective amount of an agent that increases 5-LOX levels and/or activity.

It is demonstrated herein that a decrease in 5-LOX protein and RNA is seen in the retina after injury. 5-LOX is enzyme is rate limiting for lipoxin formation but not for the neuroprotective NPD1 which has been shown to provide antiapoptotic and neuroprotective actions following oxidative stress or injury in the brain and retina (21-23). Attempts have made to restore or amplify 15-LOX activity. 15-LOX is the second enzyme in lipoxin formation. The data provided herein shows no change in 15-LOX and disappearance of 5-LOX. Accordingly agents that increase 5-LOX expression in astrocyte or glial cells may amplify or restore $LXA_4$ or $LXB_4$ formation. Activators of 5-LOX have been described including in Wisastra et al Bioorg Med Chem. 2013 Dec. 15; 21(24): 7763-7778.

As 5-LOX is required for lipoxin formation and is reduced under conditions of stress in the, the conditions and disorders described treatable by lipoxins may also be ameliorated by increasing 5-LOX levels and/or activity.

In an embodiment, the agent is a gene therapy vector that delivers 5-LOX to the retina, optionally specifically to an astrocyte or glial cell. The concept of amplifying $LXA_4$ formation by in vivo LOX gene therapy or in LOX transgenic mice has been established.

The vector can be administered by methods known in the art, and comprise a polynucleotide for 5-LOX, preferably human 5-LOX, and the components necessary for retinal, or astrocyte and/or glial expression.

Gene therapy applied directly to the retina which can be applied through intravitreal injection of AAV for example, is known the field. A retinal agent (Luxturna™) was recently approved by the FDA.

The vector can for example be a modified virus (e.g. replication defective retrovirus, adenovirus and adeno-associated virus). The vector can be adapted for specific expression in astrocytes and glial cells for example using cell specific promoters and the like (i.e. astrocyte and glial cell specific promoters, such as GFAP or Pax-2). Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. In an embodiment, the regulatory sequences direct or increase expression in neural tissue and/or cells.

In an embodiment, the vector is a viral vector.

In an embodiment, the vector is an adenovirus vector, optionally a recombinant adeno-associated virus serotype 2 (AAV2) vector, comprising a human 5-LOX cDNA, optionally with a modified Kozak sequence. The virus can be grown for example in HEK 293 cells and purified for administration.

In an embodiment, the vector comprises a cytomegalovirus (CMV) enhancer and/or a chicken beta actin (CβA) promoter driving 5-LOX expression.

Suitable systems for the transfer of genes both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome—DNA complexes. Another approach is the use of AAV plasmids in which the DNA is polycation-condensed and lipid entrapped and introduced into the brain by intracerebral gene delivery (Leone et al. US Application No. 2002076394).

Uses of the compounds, analogues and compositions described herein are also contemplated.

The compositions described herein can be prepared by per se known methods for the preparation of pharmaceutically acceptable compositions that can be administered to subjects, such that an effective quantity of the active substance is combined in a mixture with a pharmaceutically acceptable vehicle.

The compositions described herein can be administered for example, by parenteral, intravenous, subcutaneous, intramuscular, intraorbital, ophthalmic, intraocular, intravitreal, intracameral, subtenon, subconjunctival, intraperitoneal, aerosol or oral administration.

In an embodiment, the one or more lipoxin compounds or lipoxin analogues or a composition comprising said compounds or analogues is/are administered to an eye.

The compounds, analogues and/or composition may be delivered by sustained delivery devices, such as a contact lens, topical gel or ointment, polymer, or intraocular gel or sustained delivery device implant, polymer, or nanoparticles.

In yet another embodiment, the one or more lipoxin compounds or lipoxin analogues or a composition comprising said compounds or analogues is/are administered subcutaneously and/or topically.

For example, the one or more lipoxin compounds or lipoxin analogues and/or a composition comprising said compounds or analogues is/are administered using ocular administration optionally by ophthalmic dosing, topically to an eye.

In yet another embodiment, the concentration of the one or more lipoxin compounds and/or lipoxin analogues, each or in combination, is at least 50 nM and optionally less than 1 mM.

The pharmaceutical forms suitable for injectable use include sterile aqueous solutions or dispersion and sterile powders for the extemporaneous preparation of sterile injectable solutions or dispersions. Preferably, the form is sterile and fluid to the extent that easy syringability exists.

A further aspect includes a composition comprising one or more lipoxin compounds and/or lipoxin analogues, each or in combination, at a concentration of at least 0.2 nM or at least 1 nM or at least 5 nM or at least 10 nM or at least 50 nM, or at least 100 nM, or at least 200 nM, or at least 300 nM, or at least 400 nM and optionally less than 1 mM. In an embodiment the composition comprises a dose of from about 1 ng up to about 10 micrograms. Selection of the lower range of concentration or dose for a given lipoxin compound and/or lipoxin analogue or combination thereof can be determined for example based upon, e.g., the $EC_{50}$ or $ED_{50}$ of the composition in established biological assays.

In an embodiment the composition is a pharmaceutical composition.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

In an embodiment, the composition comprises a pharmaceutically acceptable carrier.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N, N,N-trimethylammonium chloride (DOTMA), diolesylphosphotidyl-ethanolamine (DOPE), and liposomes.

In an embodiment, the pharmaceutically acceptable carrier includes one or more of poly-lactide-co-glycolide (PLGA, PLA), polyesters, poly (ortho ester), poly(phosphazine), poly (phosphate ester), polycaprolactone, natural polymers, such as latex, gelatins, collagens, or polymeric blends. These can be used for example in sustained intraocular delivery systems. Such compositions should contain a therapeutically effective amount of the compound, together with a suitable amount of carrier so as to provide the form for direct administration to the patient.

In an embodiment, the composition is for use in a method or use described herein. In an embodiment, the composition, optionally a pharmaceutical composition, is for use for inhibiting or preventing retinal ganglion cell neurons (RGCs) degeneration and/or cell loss; or for use in treating and/or preventing a retinal neural disorder or retinal neural injury associated with RGC degeneration and/or cell loss.

In an embodiment, the retinal neural disorder comprises or is increased intraocular pressure (IOP) and/or glaucoma.

In an embodiment, the composition is suitably formulated for subcutaneous and/or topical administration In an embodiment, the composition is suitably formulated for administration to an eye, optionally for topical or intraocular administration.

In another embodiment, the concentration of the one or more lipoxin compounds and/or lipoxin analogues, each or in combination in the composition, is at least 0.2 nM or at least 1 nM or at least 5 nM or at least 10 nM or at least 50 nM, and less than 1 mM. In an embodiment, the dose can be about 1 ng to about 10 micrograms.

The lipoxin compound and/or lipoxin analogue is any lipoxin compound and/or lipoxin analogue described herein, including mixtures thereof.

In an embodiment, the composition is an aqueous solution with a pH in the range of 5.5 to 7.4

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

The roles and regulation of non-peptide neurotrophic factors in neuroinflammation and neurodegeneration are not well understood. Identified herein is a small molecule neuroprotective activity secreted from resting astrocytes in the inner retina, where neighboring retinal ganglion cell neurons (RGCs) are vulnerable to irreversible damage in the neurodegenerative disease glaucoma. Through metabolomic analyses it was found that lipoxins, $LXA_4$ and $LXB_4$, were strongly enriched in protective astrocyte conditioned media (ACM). Lipoxins are autacoids; specialized pro-resolving lipid mediators (SPMs) that act locally in paracrine or autocrine manners. Lipoxins were the first identified SPM, and belong to a growing family of small polyunsaturated fatty acid (PUFA) metabolites that direct potent cellular responses to dampen inflammation, resolve PMN at sites of inflammation and restore homeostasis. However, a direct activity for lipoxin signaling on neuronal homeostasis and survival has not been identified. that $LXA_4$ and $LXB_4$ are decreased in the inner retina in response to acute injury, and show that each is sufficient to produce strong neuroprotective effects in vivo. Conversely, inhibition of the rate limiting lipoxin synthetic enzyme 5-LOX, or $LXA_4$ receptor FPR2, exacerbate neuronal injury. Of the two lipoxins, $LXA_4$ bioactions and receptor signaling have been extensively investigated, while $LXB_4$'s endogenous role and mechanism of action remain to be defined. Yet surprisingly, $LXB_4$ was consistently more potent in this protective role. Experiments established that $LXB_4$ mediates a direct neuroprotective signal that is not transduced through FPR2 or the related SPM receptor GPR18. Further it is demonstrated that therapeutic treatment with $LXB_4$ is efficacious in both pathological and functional measures in a chronic glaucoma model. Together, these results indicate that astrocyte secreted lipoxins $LXA_4$ and $LXB_4$ have novel direct neuroprotective actions that are impaired following neuronal injury. Restoration of this intrinsic activity identifies a potential new therapeutic target for treating neurodegeneration. Details of the experiments performed are provided in Example 2.

Example 2

Non-cell autonomous signaling has been strongly implicated in metabolic and biomechanical RGC damage and parainflammation (4, 37), with emphasis on the role of toxic TNF-α secreted by reactive astrocytes (38-41). Inhibition of this mechanism promotes RGC survival following acute injury (42). However, induced glial reactivity in this context was not, by itself, sufficient to induce RGC death (42), suggesting that a concomitant loss of protective activity may also be involved. Yet, the nature of this glial-derived protective signal has not been clear. To address this question an established model of cultured retinal astrocytes (43, 44) was used to investigate a secreted neuroprotective signal generated by these cells. Further characterization surprisingly revealed that a small molecular-weight fraction contributes a substantial portion of this activity. Through metabolomic analyses the lipoxins, $LXA_4$ and $LXB_4$, were identified as highly enriched in the protective astrocyte conditioned media (ACM).

The identification of highly enriched $LXA_4$ and $LXB_4$ in neuroprotective ACM, and of their regulation in the inner retina in response to acute injury is described. Each lipoxin is sufficient to produce strong neuroprotective effects in vivo. Conversely, inhibition of 5-LOX, or FPR2, exacerbate neuronal injury. Surprisingly, $LXB_4$ shows consistently higher neuroprotective activity than $LXA_4$, and further in vitro analysis demonstrates that it mediates a direct neuroprotective signal that is not transduced through established receptors. Further therapeutic treatment with $LXB_4$ is efficacious in both pathological and functional measures in a chronic glaucoma model. Together, these results indicate a novel intrinsic neuroprotective role for astrocyte secreted lipoxins, particularly $LXB_4$, which is impaired by retinal stress or injury. Restoration of this activity identifies a new therapeutic target for treatment of neurodegenerative diseases.

Materials and Methods

Mouse Acute Retinal Insult Model

Male C57BLL/6 mice, 4-6 weeks of age, were purchased from Taconic or Jackson labs. All experimental protocols were approved by the UHN and UC Berkeley ACUC in accordance with applicable regulations. Mice were anesthetized by intraperitoneal injection of ketamine/xylazine. Intravitreal injections with 10 mM kainic acid (KA) were performed as previously described (45). Briefly, a 30-gauge needle was inserted tangentially into the vitreous and replaced with a Hamilton syringe to inject a volume of 2 µL, followed by application of ophthalmic antibiotic ointment (BNP, Vetoquinol). In some experiments, 10× concentrated ACM or test compounds were injected intravitreally one hour prior to the KA injection in concentrations as follows: $LXA_4$ and $LXB_4$ at 10 µM, Zileuton at 2 µg/ul, and WRW4 at 15 µM, all dissolved in PBS. Mice were euthanized by $CO_2$ asphyxiation 18 hours post KA treatment and the eyes fixed in 4% paraformaldehyde. In all experiments n refers to the number of animals tested.

Astrocyte and RGC Cultures

For astrocytes: Primary mature retinal astrocytes (RA) were isolated and cultured as previously described (46). Briefly, eyes were dissected out of adult Wistar rats and placed in ice-cold MEM-H17 media. Isolated retinas were digested by shaking in MEM-H17 containing papain and DNAse, followed by trituration to disperse cell-aggregates. When cultures reached confluence, the cells were placed on a rotating shaker for 6-8 hours to remove microglia and then re-plated. A glial-specific expression profile was confirmed by probing the cultures with a panel of glia microglia and neuronal markers (44). For RGCs: RGCs were purified using magnetic MicroBeads (Miltenyi Biotec, Germany) according to the manufacturer's protocol. Briefly; retinal cell suspensions were prepared from 8-10 day old rats and incubated with CD90.1 microbeads, and then carefully washed with DPBS/BSA buffer. The suspension was centrifuged at 130×g and the supernatant aspirated. Cells were then incubated with biotinylated depletion antibodies against microglia and endothelial cells. The labeled cell suspension was then incubated with magnetic Anti-Biotin MACSiBead™ Particles, and placed in a weak magnetic field. The pre-enriched cell suspension was centrifuged, and resuspended in fresh DPBS/BSA buffer and applied to a MACs MS separation column in the presence of a strong magnetic field to select for CD90.1-bound RGCs. To increase RGC purity, the eluted fraction was enriched over a second column. Purified RGCs were eluted and plated on poly-D-lysine coated dishes. The cells were cultured in Neurobasal-A media (Gibco) supplemented with 2% calf serum, B27, L-glutamine, BDNF, CNTF, forskolin and pen/strep.

LC-MS/MS

Eicosanoids and PUFA in the conditioned media were quantified via liquid chromatography-tandem mass spectrometry (LC-MS/MS) according to the published protocol (34, 47-49). Briefly; class specific deuterated internal standards ($PGE_2$-d4, LTB4-d4, 15-HETE-d8, $LXA_4$-d5, DHA-d5, AA-d8) were used to calculate extraction recovery on an LC/MS/MS system consisting of an Agilent 1200 Series HPLC, Kinetex C18 minibore column (Phenomenex), and AB Sciex QTRAP 4500 system. Analysis was carried out in negative ion mode, and eicosanoids and PUFA were quantitated using scheduled multiple reaction monitoring (MRM) using 4-6 specific transition ions for each analyte. Calibration curves were established with synthetic standards (Cayman Chemicals).

Quantitative rt-PCR

Mouse retinal mRNA was isolated using RNeasy isolation kit (Qiagen), quantified using NanoDrop, and mRNA reverse transcribed with High Capacity cDNA kit (Applied Biosystems). q-PCR was performed with SYBR Green Master Mix (Applied Biosystems) using the ΔΔcT method in a Step One Plus qPCR system (Applied Biosystems). β-actin was used as the reference gene.

Immunofluorescence Microscopy

Following fixation eyes were equilibrated in 30% Sucrose for 12 hours, embedded in OCT, and cryosectioned. Sections were blocked and probed with primary antibodies to GFAP (Sigma), CD68, GR-1 and F4/80 (Biolegend), FPR2 (Abnova), RBPMS (Phosphosolutions), BRN3a (Santa Cruz), 5-LOX (Millipore), according to standard protocols. Following PBS-t washes, sections were incubated with fluorescent-conjugated secondary antibodies (Molecular Probes) and mounted with glycerol-based medium containing DAPI. TUNEL staining was performed according to the manufacturer's instructions (DeadEnd; Promega). Briefly, sections were fixed with 4% PFA for 5 minutes and washed in PBS. Equilibration buffer was added, and rTdT reaction mix was applied to each slide and incubated at 37° C. for 60 min. Slides were immersed in 2×SSC and then washed with PBS. This was followed by blocking with 5% goat serum and overnight incubation with primary antibodies at 4° C. Immunofluorescent images were acquired with a Zeiss Axio-Imager microscope and confocal images were acquired with Nikon Eclipse-Ti confocal microscope.

Quantification of RGC Survival

To quantify the extent of apoptosis, a well-established method was used to count the number of TUNEL-positive nuclei in the ganglion cell layer (GCL) and expressed it as a fraction of the total GCL nuclei (50-54). TUNEL labeling was performed according to the manufacturer's instructions (DeadEnd; Promega). Briefly, cryostat sections were fixed with 4% PFA for 5 minutes and washed in PBS. Equilibration buffer was added, and rTdT reaction mix was applied to each slide and incubated at 37° C. for 60 min. Following the rTdT reaction, slides were washed in 2×SSC and PBS and finally mounted with glycerol-based medium. For RGC survival, RBPMS-positive cells in the GCL were counted and expressed as a fraction of GCL nuclei. For each eye, at least five central retinal sections were analyzed at the level of the optic nerve stretching to each ora serrata, and the results averaged, as previously described (42).

Rat Chronic IOP Model:

A method for reliably inducing sustained IOPs in the rodent eye was recently developed by Liu et al (55, 56). In this minimally invasive approach, a circumlimbal suture is placed to induce chronic ocular hypertension. An advantage of this strategy is that specific IOPs can be targeted and monitored by rebound tonometry, improving the consistency of results. In addition, following suturing elevated IOPs can be maintained for as long as 15 weeks (55). The model reproduces key features of glaucoma, such as; progressive and preferential decline in RGC function starting by week 8, gradual loss of the retinal nerve fiber layer (RNFL) by week 12, and RGC death by week 15, with minimal overt inflammation (55, 57). In the experiments, circumlimbal sutures were placed in the randomized right or left eyes of anesthetized rats using a sterile 8-0 nylon suture. IOP was measured twice a week, and only animals showing sustained elevated IOP over 21 mmHg for the duration of the experiment were included in the analyses. The delivery and dosage of $LXB_4$ was based on previous publications (58-60). Briefly, $LXB_4$ or vehicle were administered starting from week 8 on alternate days. Due to the unstable nature of lipoxins, a hybrid approach was taken to ensure consistent delivery, including both IP delivery (1 μg) and topically to each eye (100 ng). ERG was measured monthly to assess RGC functional changes using the positive scotopic threshold response (pSTR), which has been used to measure the impact of elevated chronic IOP in rats (55, 61). In addition, RNFL and total retinal thickness were quantified once a month using optical coherence tomography (OCT). After 15 weeks, animals were euthanized and RGC numbers were counted on middle and peripheral quadrants of retinal flatmounts following immunofluorescent staining for the RGC marker BRN3a as above.

Statistical Analyses

For all experiments n refers to the number of animals or biological replicates (in vitro). For TUNEL staining and RGC counts statistical analyses were performed by t-test or one-way ANOVA with TUKEY post-hoc analyses as appropriate. ERG and OCT results were analyzed by two-way ANOVA with Bonferroni post-hoc test. For figures the number of asterisks generally refers to *p<0.05, p<0.01, and *p<0.005.

Results

Figure 9A:
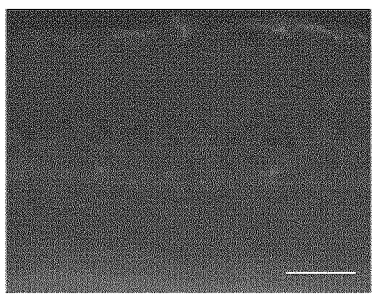
FIG. 9A to 9I are images showing that transplanted retinal astrocytes do not induce endogenous reactivity or inflammation.
Figure 9B:
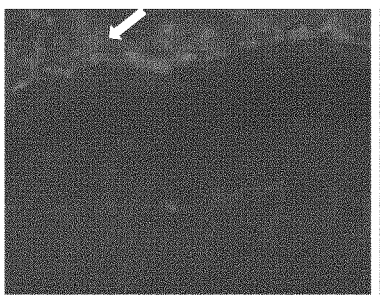
Figure 9C:
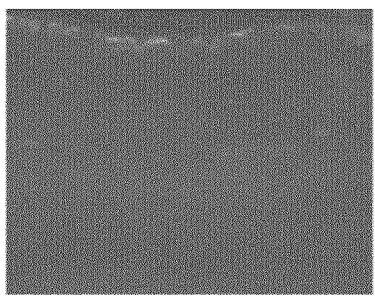
Figure 9D:
Figure 9E:
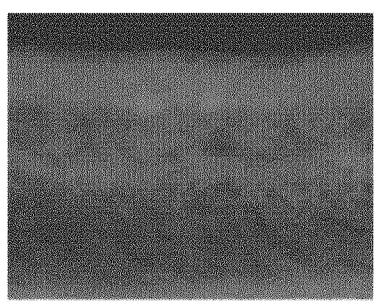
Figure 9F:
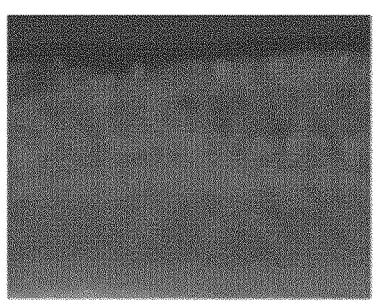
Figure 9G:
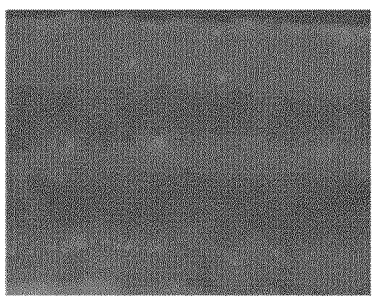
Figure 9H:
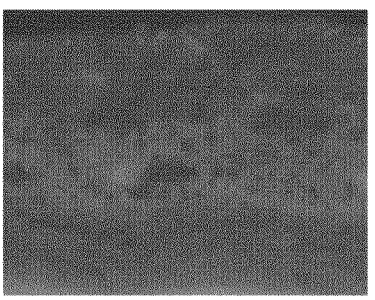
Figure 9I:
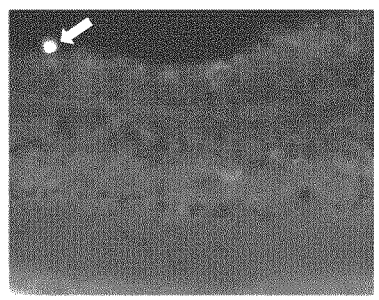
Figure 11A:
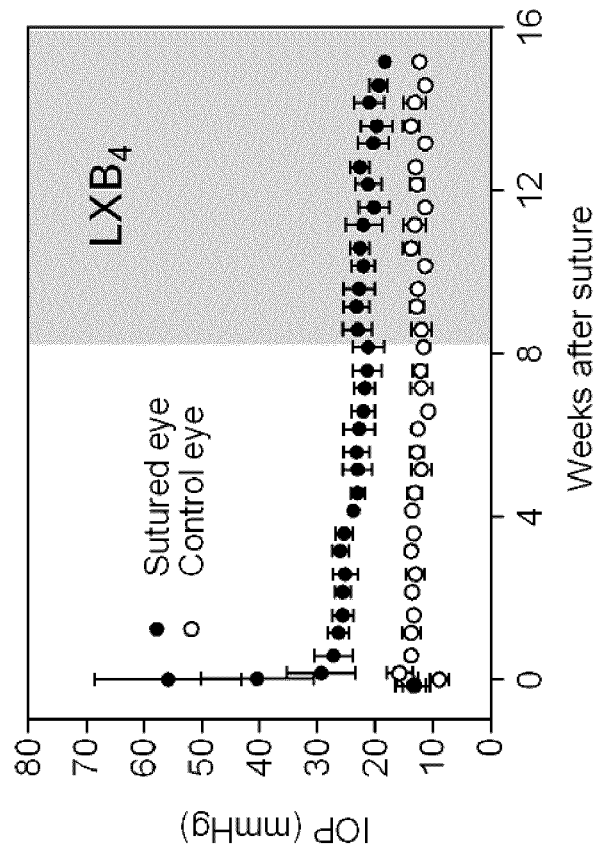
FIG. 11A-FIG. 11B are graphs that show that LXB$_4$ treatment had no effect on IOP compared to vehicle treatment. IOPs were measured twice weekly throughout the suture model study. The shaded area indicates the period of LXB$_4$ or vehicle treatment (n=8 for each group; error bars=SD).
Figure 11B:
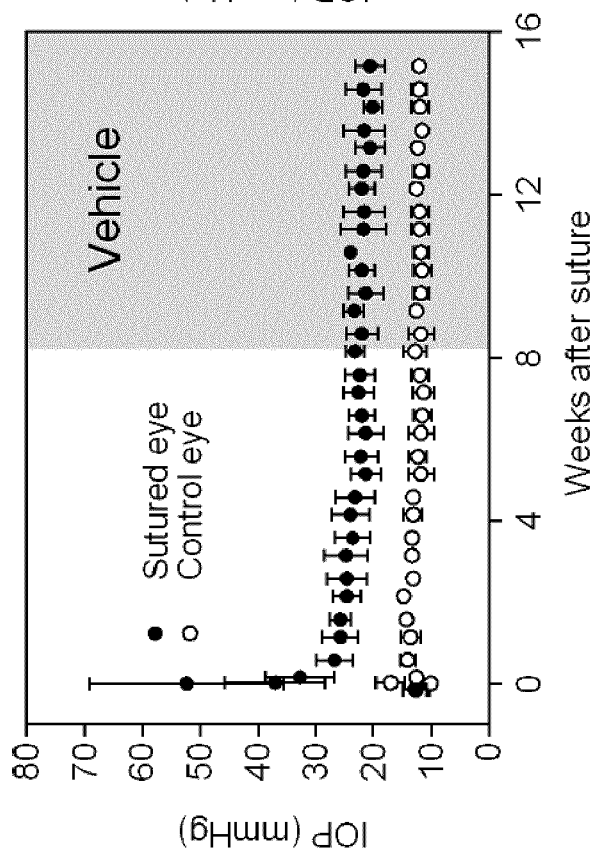

Transplanted retinal astrocytes have specific neuroprotective activity that is compromised by stress. In vitro models of mature astrocytes isolated from the adult rodent and human retina and optic nerve head have been extensively characterized (42, 44, 46, 54, 62). These cells display typical astrocyte morphology, and a variety of appropriate markers, including GFAP, vimentin, Pax-2, GS, and S100A, and they robustly respond to oxidative and metabolic stress with p38 MAPK-dependent changes in activation markers, secreted cytokines, and antioxidants (44) (FIG. 8A-FIG. 8E). Using this protocol, the effects of rat retinal astrocytes (RA's) on inner retinal neurons was studied by transplanting them into recipient eyes. For these experiments 100,000 RAs, or vehicle, were injected intravitreally into C57BL/6 eyes. Recipient retinas were evaluated histologically after 16 days, and showed minimal endogenous glial activation, inflammatory infiltrates, or cell death (FIG. 9A-FIG. 9I). Furthermore, injection of GFP expressing RA's (Ad-GFP) showed that transplants were intact and viable, maintained GFAP immunoreactivity, and did not invade, the retina (FIG. 9B, FIG. 9D).

Figures 1D, 1E, 1F:
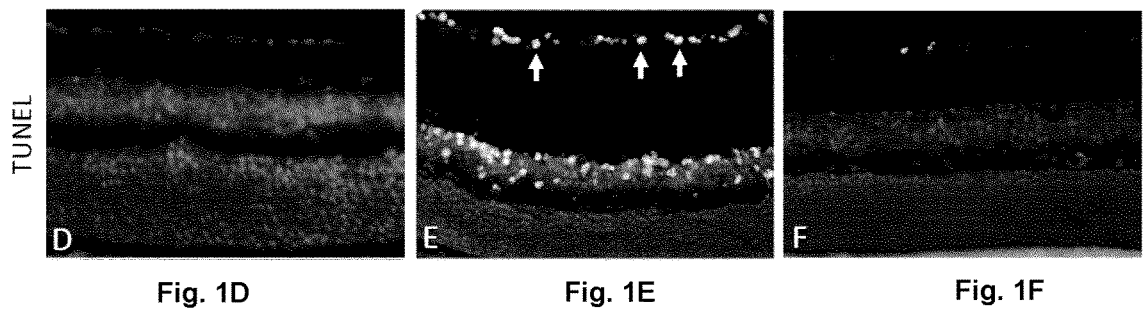
FIG. 1D-FIG. 1F are adjacent sections stained for TUNEL signal (arrows), which show a complementary pattern of apoptosis in the GCL and INL, which was reduced in eyes with transplanted RAs.
Figures 1G, 1H, 1I, 1J:
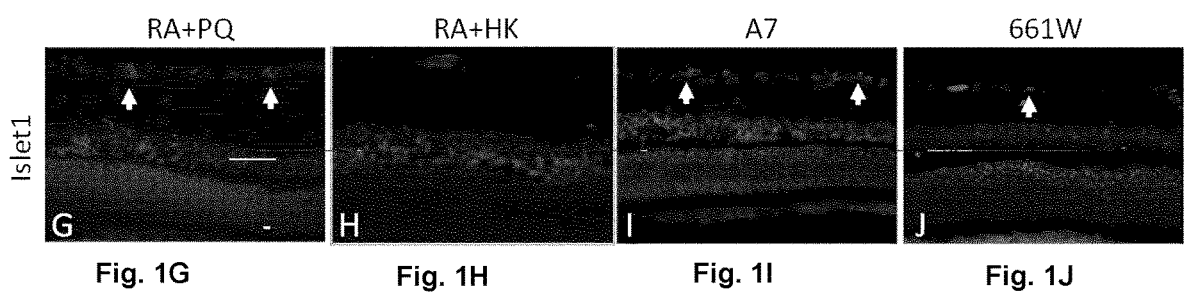
FIG. 1G-FIG. 1J shows rescue of Islet1 positive neurons was reduced or absent when RAs were pre-stressed by treatment with 300 μM PQ (RA+PQ), or heat killed (RA+HK) (FIG. 1G, FIG. 1H, respectively, bar indicates 50 μm). Likewise, transplants of A7 or 661W cells were not protective (FIG. 1I, FIG. 1J, respectively).
Figures 1K, 1L, 1M, 1N:
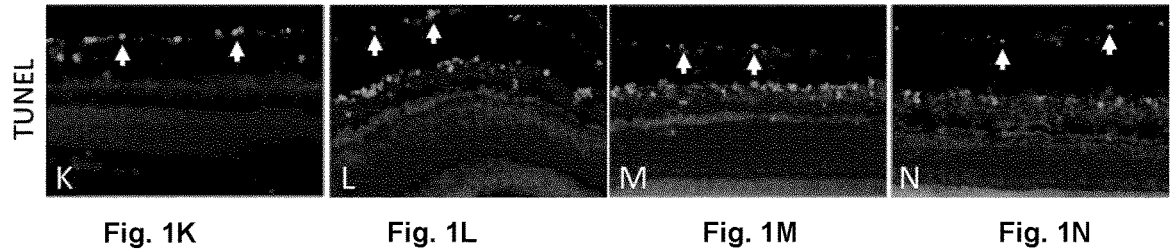
Figure 1O:
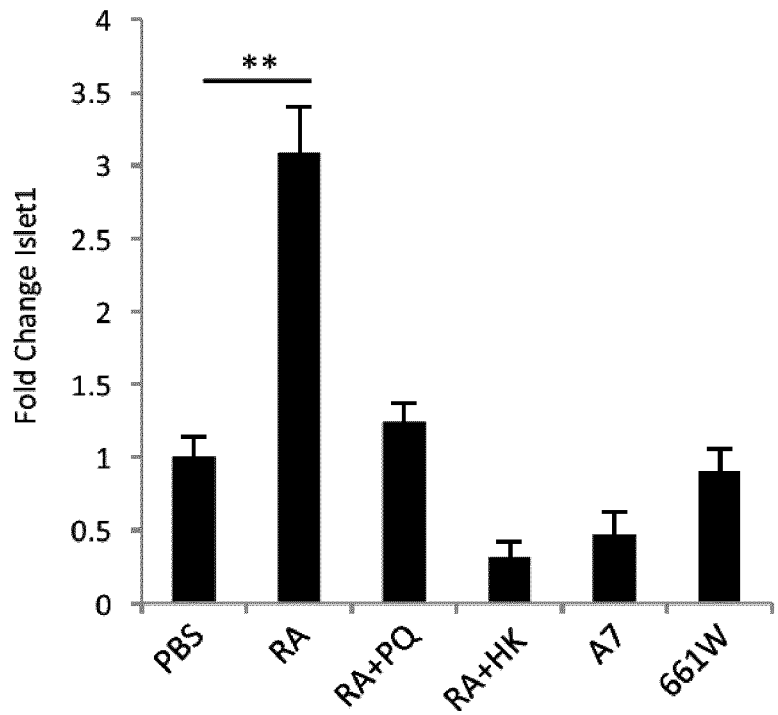
Figure 1P:
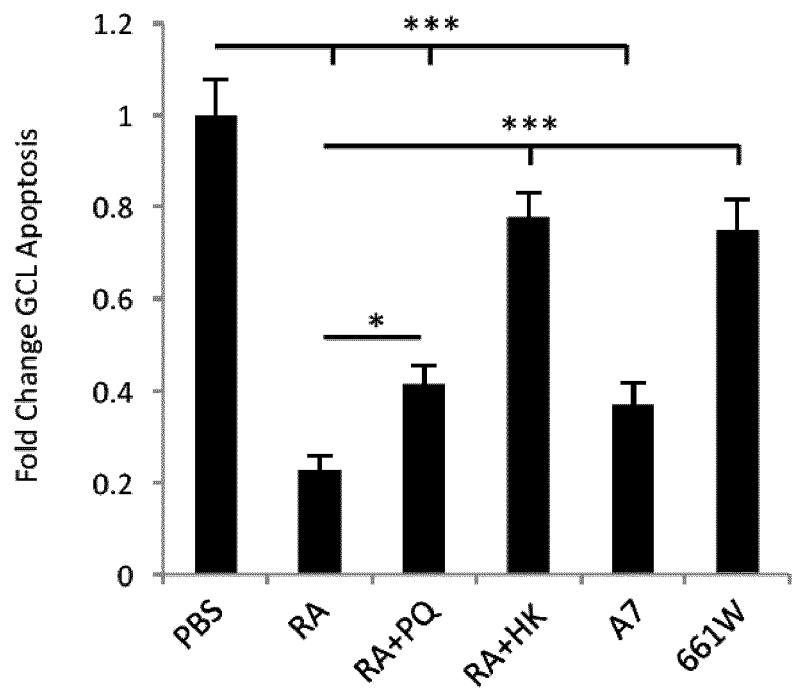

In order to test the influence of the transplanted cells on inner retinal pathology, RA's were transplanted as above. After 16 days retinas were challenged with an acute metabolic injury by injection of kainic acid (KA). Similar excitotoxic injury models have been previously extensively used to study the influence of retinal glia on neuronal survival and function, providing a consistent and accurate assessment of retinal neuropathology (39, 42, 54, 63-65). Remarkably, RA transplants strongly protected neurons in the ganglion cell layer (GCL) from KA induced loss, as shown by probing for the RGC and amacrine marker Islet-1 (FIG. 1A-FIG. 1C). In complementary studies, TUNEL staining for apoptotic cells showed a marked reduction of apoptotic cells in transplanted eyes compared to PBS injected controls (FIG. 1D-FIG. 1F). As further controls, prior to injection RA's were exposed to oxidative stress with the redox agent paraquat (PQ) (FIG. 1G), which is a redox cycling agent that generates reactive oxygen species and induces activation and stress markers (44), or heat killed to control for generalized inflammatory effects (FIG. 1H). Neither treatment was effective at rescuing GCL neurons, nor was injection of the immortalized optic nerve astrocytic cell line A7 (FIG. 1I), or retinal neuronal cell line 661W (FIG. 1J). Complementary results were likewise obtained through TUNEL staining (FIG. 1 K-N). Quantification of these results revealed that eyes transplanted with RAs showed a significant three-fold rescue of GCL neurons compared to PBS, but that protection of the various controls was absent or reduced (FIG. 1O, FIG. 1P). Therefore, these experiments suggested that RAs actively provide neuroprotective support that may be compromised following stress or injury.

Retinal astrocyte neuroprotection is mediated through secreted factors that include a small molecule component enriched in $LXA_4$ and $LXB_4$. The protective activity induced by transplanted RAs could be driven by an endogenous detoxifying mechanism, or it could be accomplished through secreted signals. In order to distinguish between these possibilities, astrocyte conditioned media (ACM) was collected, to test whether it was sufficient in reproducing protective activity. Concentrated ACM was injected into the vitreous of C57/Blk6 mice 24 hours prior to challenge with KA. This time, survival of RGCs was specifically assessed by probing for the selective marker RBPMS, along with complementary TUNEL staining, and quantified as previously. As expected, extensive RGC loss was detected in KA challenged eyes injected with cell-free control media incubated under the same conditions as ACM (FIG. 2A). However, significant rescue of RGCs was observed in eyes injected with ACM (FIG. 2A, FIG. 2B). Conversely, TUNEL staining showed a complimentary result whereby ACM induced reduction in GCL apoptosis (FIG. 2C, FIG. 2D).

An in vitro assay to recapitulate key aspects of the acute KA model was established. In this case, unconcentrated ACM was applied to the glutamate sensitive neuronal cell line HT22 (66, 67). Glutamate challenge of 5 mM was titrated to induce 60-80% cell death (ie: 20-40% survival). Consistent with the in vivo results, ACM treatment produced significant HT22 cell protection (FIG. 2E). These data established a platform for future studies of the ACM activity. The media was concentrated for proteomic analyses. Interestingly, however, it was found that a major portion of the protective activity was contained in a fraction smaller than 3 kDa (FIG. 2F), suggesting that small molecules made up a substantial component of the ACM activity.

In order to identify small molecules enriched in the ACM that might account for the neuroprotective activity, metabolomic analyses were performed, including an assessment of SPMs using liquid chromatography-tandem mass spectrometry (LC/MS/MS) based lipidomics. Lipid mediators released in the media were quantified to generate a lipidomic profile of SPMs, including eicosanoids and PUFAs (34, 47-49). Pathway markers for DHA derived resolvins and protectins were detected (DHA, 17-HDHA) but not their direct formation. In contrast, lipidomic analyses revealed a prominent enrichment of the lipoxins $LXA_4$ and $LXB_4$ in ACM compared to control media (FIG. 2G).

Figure 3A:
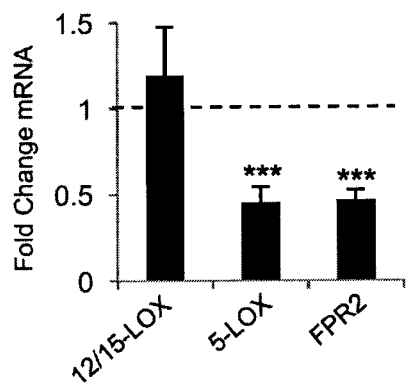
FIG. 3A to FIG. 3G is a graph and series of images showing that lipoxins are regulated in the inner retina in response to acute injury.
Figure 3B:
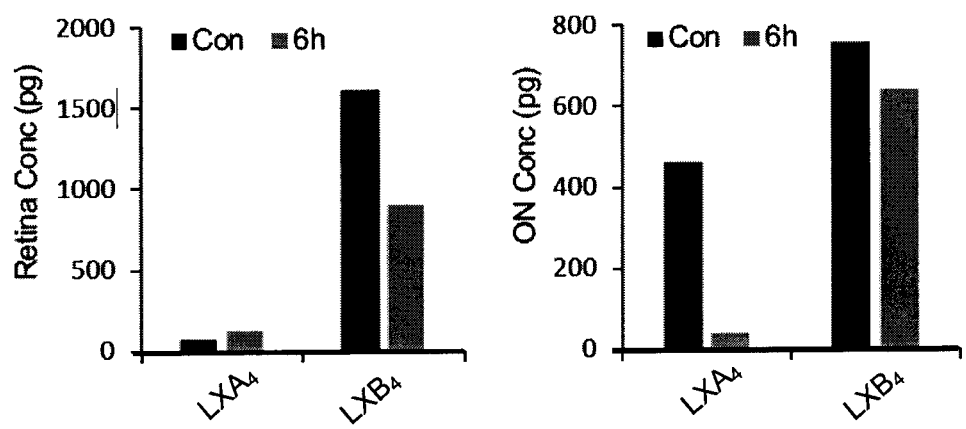

$LXA_4$ and $LXB_4$ synthesis and signaling are regulated in the inner retina. In order to corroborate the presence of lipoxin signaling in the retina, the expression of the lipoxin synthetic enzymes 5-LOX and 12/15-LOX (the mouse ortholog of 15-LOX (68)), as well as the established $LXA_4$ receptor, FPR2, was assessed in the mouse retina. All three transcripts were detected by quantitative rt-PCR (qPCR) (FIG. 3A). Interestingly, expression levels of 5-LOX and FPR2, but not 12/15-LOX, were significantly reduced following retinal insult (FIG. 3A).

Figure 3C:
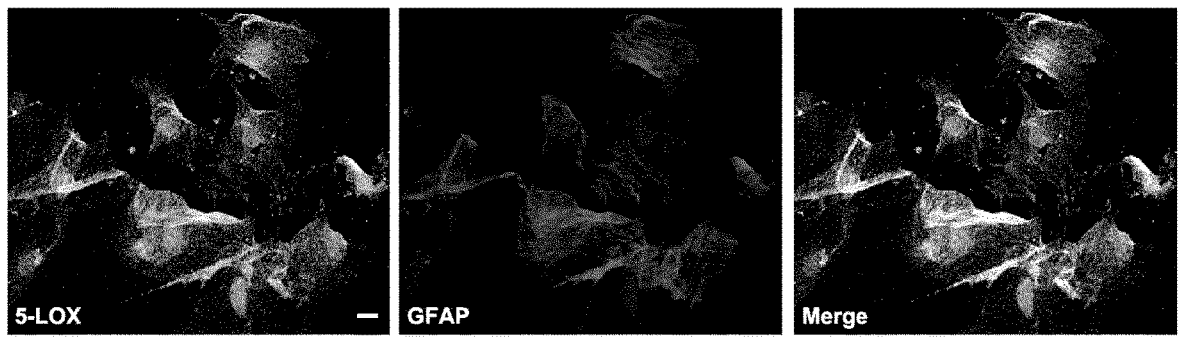
Figure 3D:
Figure 3E:
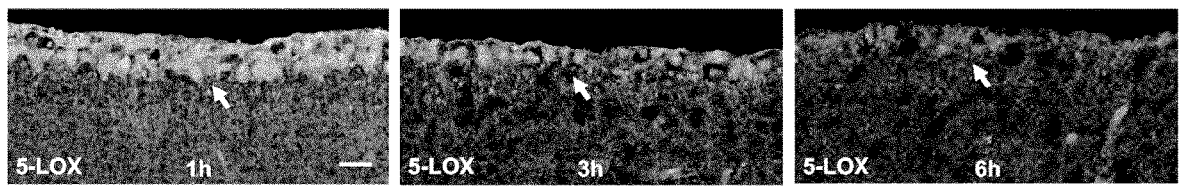
Figure 3F:
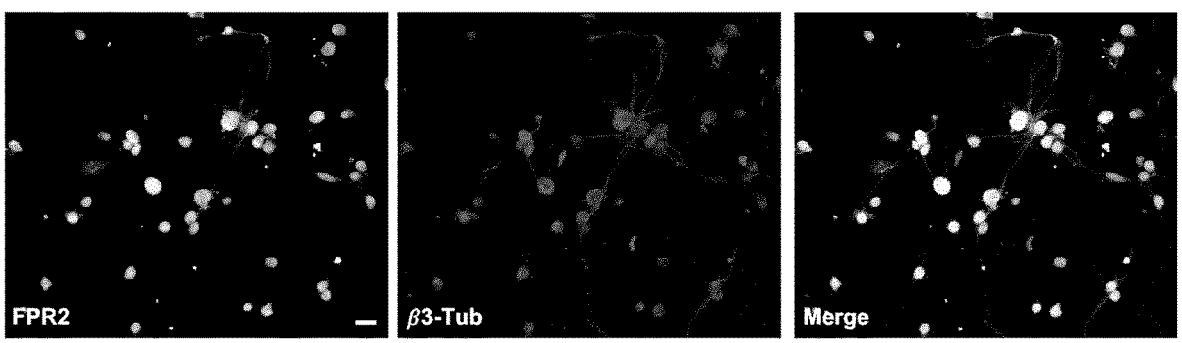
Figure 3G:

5-LOX is the rate limiting enzyme for $LXA_4$ and $LXB_4$ formation and histology confirmed the protein expression in cultured RAs (FIG. 3C) and localized expression in the inner retina in astrocytes and RGCs (FIG. 3D). Consistent with the qPCR results, retinal insult reduced the 5-LOX signal by three and six hours post injury (FIG. 3E). In comparison, immunostaining demonstrated FPR2 protein in RGCs in vitro and in vivo. (FIG. 3F, FIG. 3G). These data suggest that the lipoxin circuit, comprised of biosynthetic enzymes and receptor, is present in the inner retina, and that their production is reduced in response to acute injury.

Figure 4A:
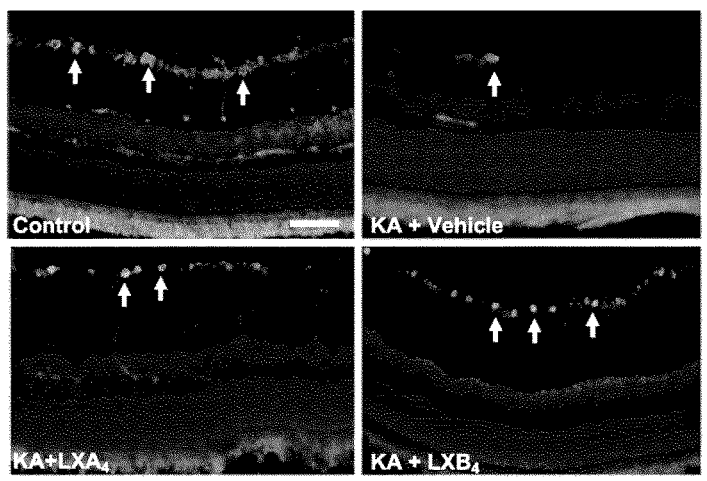
FIG. 4A to 4F is a series of images and graphs showing that $LXA_4$ and $LXB_4$ promote RGC survival following acute injury.
Figure 4B:
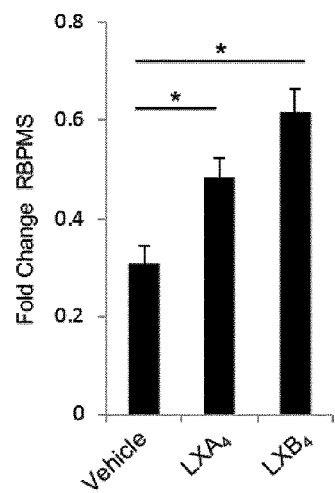

$LXA_4$ and $LXB_4$ promote RGC survival following acute insult. Treatment with $LXA_4$ or $LXB_4$ was assayed to determine if it is sufficient to promote RGC neuroprotection in vivo. To test this 2 µl of 10 µM synthetic $LXA_4$ or $LXB_4$ were injected intravitreally, one hour prior to retinal KA insult. RGC survival was quantified as previously. Both $LXA_4$ and $LXB_4$ treatments significantly increased RGC survival by 37% and 50%, respectively compared to vehicle control (FIG. 4A, FIG. 4B). Unexpectedly, $LXB_4$ was the more efficacious molecule (stats, support important statement), when directly compared to LXA$_4$, which has well-documented and potent anti-inflammatory and proresolving actions in vivo and in vitro.

Figure 4C:
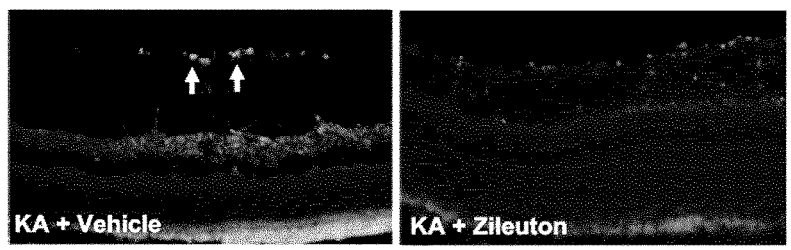
Figure 4D:
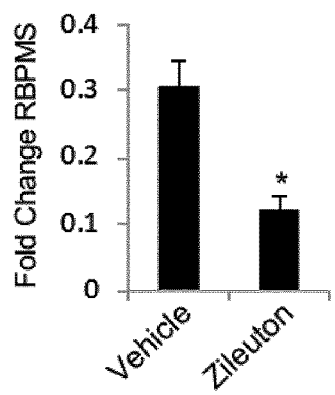
Figure 4E:
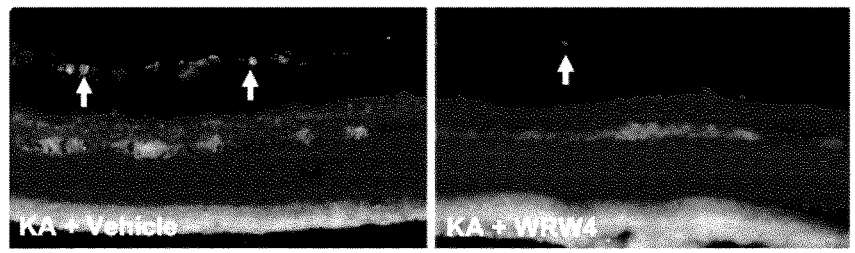
Figure 4F:
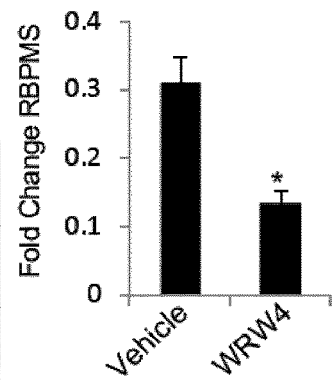

As an alternative approach to confirm the role of endogenous lipoxin signaling, w Zileuton, a selective inhibitor of 5-LOX activity that is used clinically (34, 69, 70) was administered. Intravitreal administration of Zileuton alone had no effect on RGC numbers (FIG. 10A-FIG. 10D), but significantly exacerbated RGC loss in response to KA challenge by 60% (FIG. 4C, FIG. 4D). These results indicate that 5-LOX activity regulates endogenous neuroprotective activity. In order to further establish that lipoxin signaling mediates neuroprotection, WRW4, a selective FPR2 inhibitor (70-72) was administered. Similar to 5-LOX inhibition, FPR2 antagonism had no effect on RGC survival alone (FIG. 10A-FIG. 10D). However, intravitreal WRW4 increased acute RGC loss by 67% compared to vehicle (FIG. 4E, FIG. 4F). Together, these data demonstrate that lipoxin biosynthetic pathways and receptors are intrinsic factors for neuroprotection from an acute stress challenge, and that their inhibition exacerbates neuronal damage.

Figure 5A:
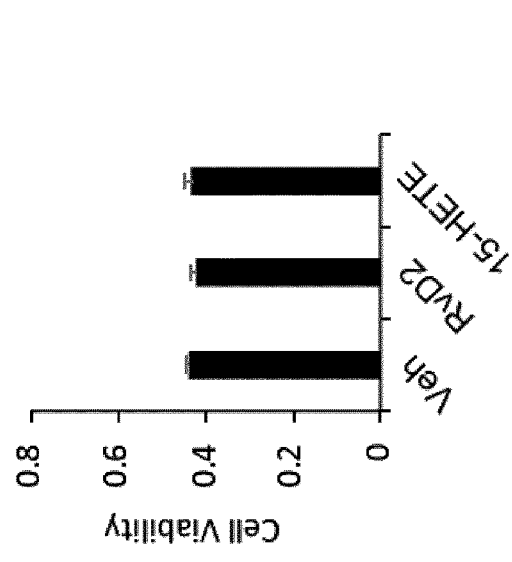
FIG. 5A to FIG. 5L is a series of images and graphs showing that $LXA_4$ and $LXB_4$ have direct neuroprotective activities.
Figure 5B:
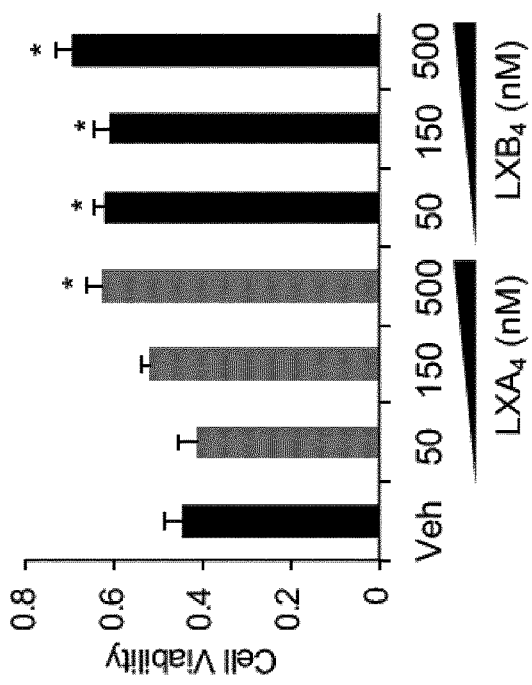

LXA$_4$ and LXB$_4$ promote direct neuroprotective signaling. To the inventor's knowledge, a role for lipoxins as direct neuroprotective or neurotrophic factors has not been reported. Although their established anti-inflammatory actions extend to the CNS (29-32). However, it was hypothesized they may have indirect protective effects. In order to test whether the protective activity was direct or indirect, LXA$_4$ or LXB$_4$ was applied to neuronal cells in an established in vitro assay. Increasing concentrations of LXA$_4$ or LXB$_4$ produced significantly increased viability of glutamate challenged HT22 cells (a glutamate sensitive hippocampal neuronal cell line), demonstrating a direct protective action (FIG. 5A). Consistent with in vivo results, LXB$_4$ was more potent, showing more activity than LXA$_4$, at concentrations as low as 50 nM (FIG. 5A).

Figure 5C:
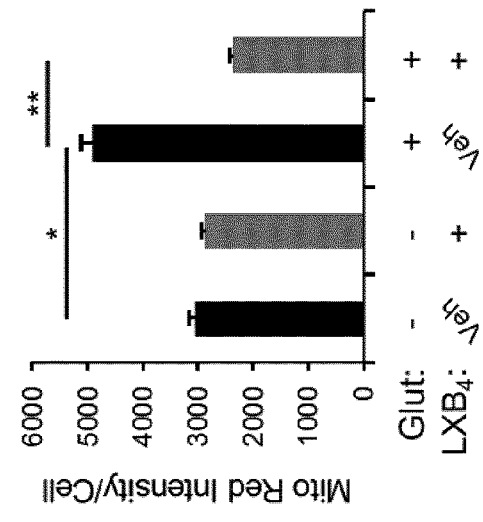
Figure 5D:
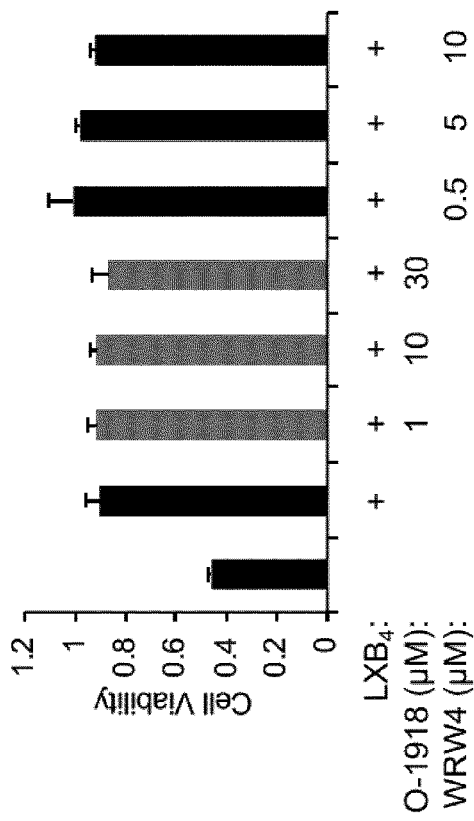

LXB$_4$ and LXA$_4$ are inactivated by the same mechanism (73), but do not mediate their action via the same receptor or signaling mechanism (25, 28). Hence, the more potent activity for LXB$_4$ with neurons suggests distinct mechanisms of action for LXA$_4$ and LXB$_4$. There is no established receptor for LXB$_4$. However, LXB$_4$ shares structural homology with LXA$_4$ and the DHA-derived resolving D2 (RvD2), which mediate their actions via FPR2 or GPR18 (74), respectively. Therefore, it was assessed whether specific receptor antagonists for FPR2 or GPR18 could block LXB$_4$ mediated protection. Increasing concentrations of WRW4 (FPR2 antagonist), or O-1918 (GPR18 antagonist), did not block LXB$_4$ protective activity in HT22 cells (FIG. 5C). These data suggest that LXB$_4$ neuroprotection is specific, and mediated through a signaling mechanism that is distinct from LXA$_4$, and does not act through the a receptor for the structurally related RvD2.

Figure 5E:
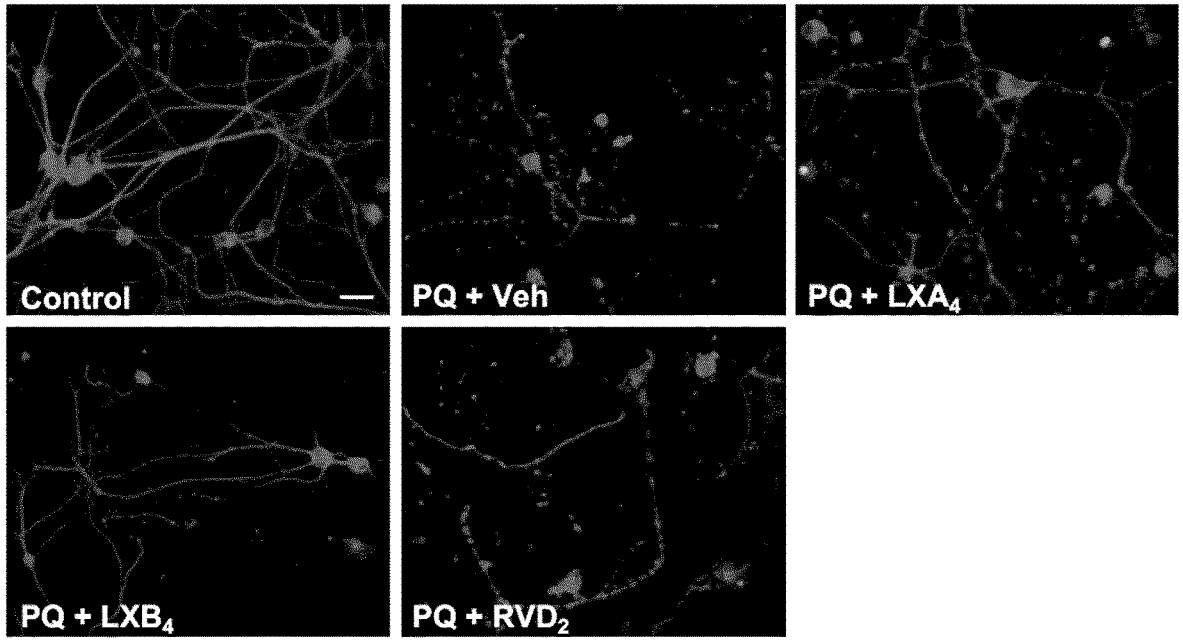
Figure 5F:
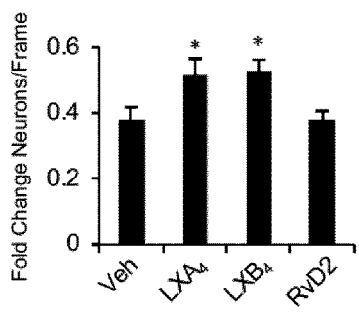
Figure 5G:
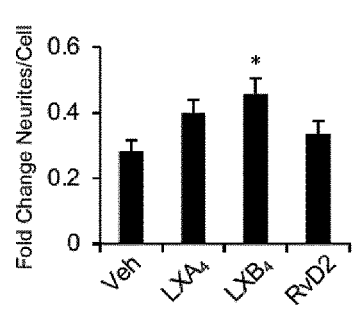
Figure 5H:
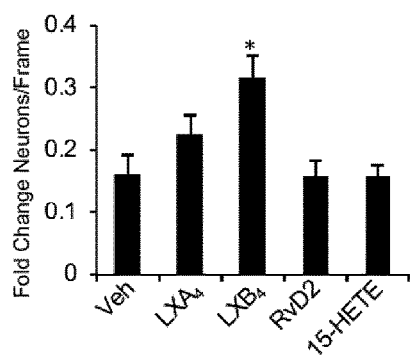
Figure 5I:
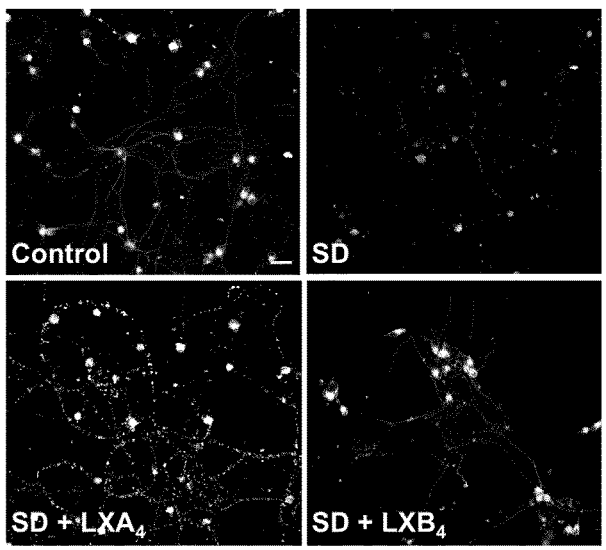
Figure 5J:
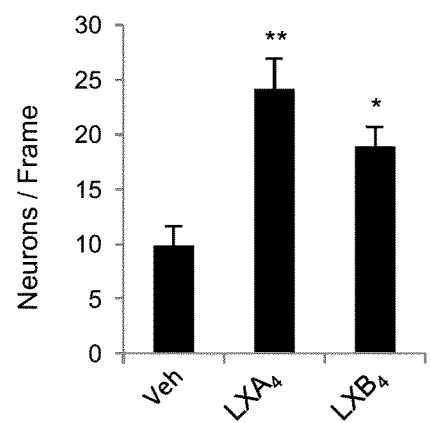
Figure 5K:
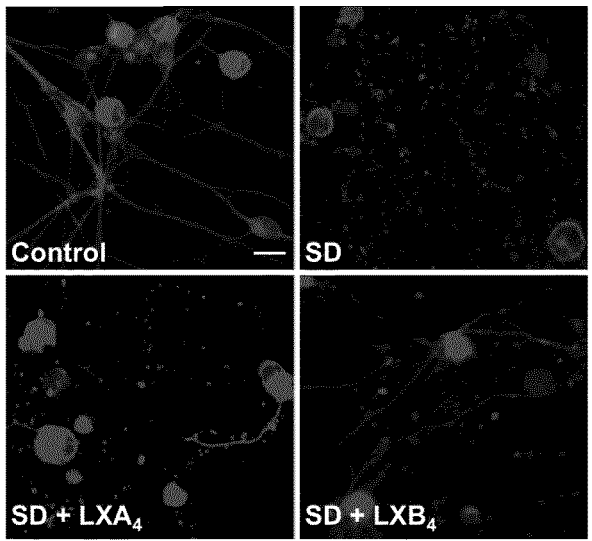
Figure 5L:
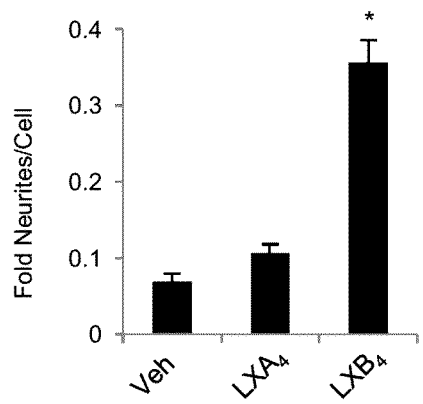

To further confirm direct lipoxin activity in primary neurons, the ability of LXA$_4$ or LXB$_4$ to protect primary RGCs was tested. RGCs were isolated by immunopanning according to established methods. The cells were subjected to serum deprivation (SD), and then stained for β3-tubulin to quantify cell and neurite survival. Under normal serum, the RGCs extended an extensive network of neurites. However, after 48 h of SD the neurite and cell numbers were dramatically reduced (FIG. 5E, FIG. 5F, FIG. 5). Treatment with 1 μM of either LXA$_4$ or LXB$_4$ significantly rescued RGC numbers (FIG. 5E, FIG. 5F). However, only LXB$_4$ significantly rescued neurite degeneration (FIG. 5G, A similar significant rescue of cell survival was observed in primary cortical neurons (FIG. 5H), providing further evidence that LXB$_4$, and to a lesser extent LXA$_4$, have direct and distinct actions in neurons.

Figure 6A:
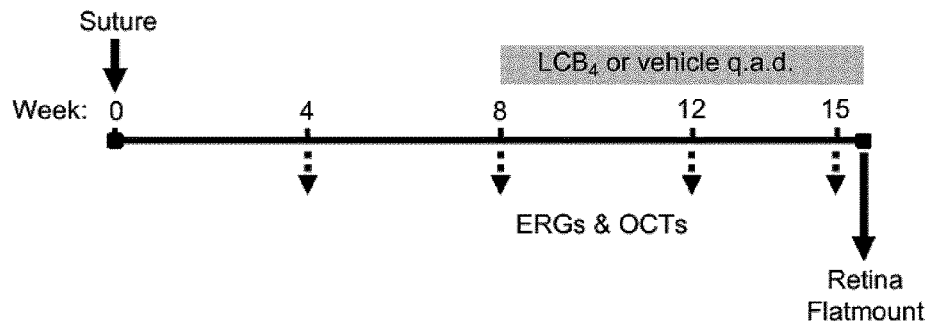
FIG. 6A is a schematic of the experimental design showing ERG and OCT readings every 4 weeks following suture induced IOP. $LXB_4$ administration started at week 8, and retinal flatmounting and RGC counting was performed at week 15.

Therapeutic LXB$_4$ treatment rescues RGC function in a chronic IOP dependent glaucoma model. To assess whether LXB$_4$ action extends beyond acute stress models, it was investigated if it provides RGC protection in a chronic model more relevant to human neurodegenerative disease. For this purpose a recently described rat perilimbal suture model of glaucoma was used, in which moderately elevated intraocular pressure (IOP) can be consistently maintained over 15 weeks (55, 57). Elevated IOP is the primary clinical glaucoma risk factor, and this model results in similar compromised RGC function, reduced nerve fiber layer (NFL) thickness, and death of RGCs by week 15 (55). Interestingly, suture removal up to 8 weeks results in reversal of elevated IOP and RGC functional recovery (57). Therefore, this time point was chosen to initiate an experiment in which therapeutic treatment with LXB$_4$ or vehicle was administered to sutured rats starting at week 8, with longitudinal and pathological assessment of RGC function and survival (FIG. 6A).

Figure 6B:
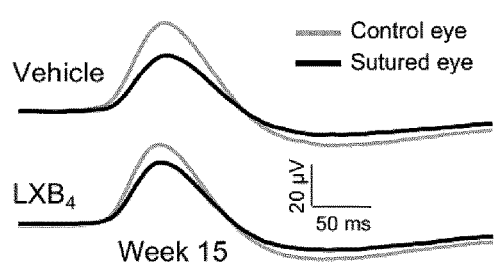
FIG. 6B is a graph showing average waveforms for RGC (pSTR) responses at week 15 for LXB$_4$ and vehicle groups.
Figure 6C:
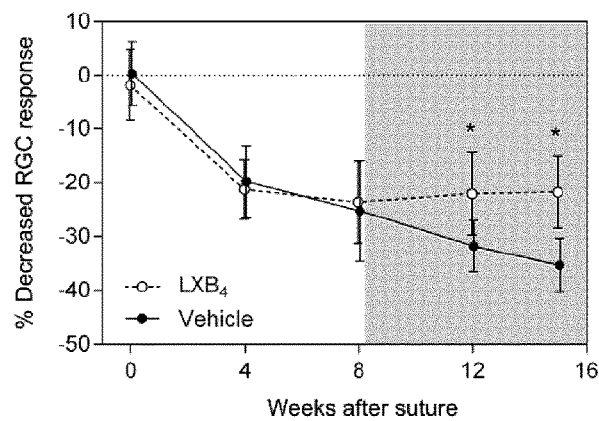
FIG. 6C is a graph that shows the relative change in RGC function across 15 weeks. Starting at week 12, there was a significant and increasing rescue of LXB$_4$ treated eyes compared to vehicle (*p<0.05; ***p<0.005; n=8 per group, bars are S.D., the shaded area indicates the treatment period).
Figure 6D:
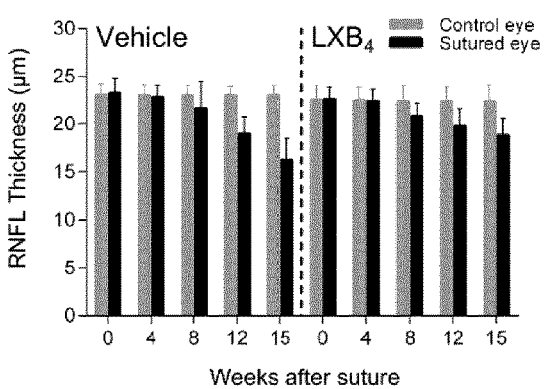
FIG. 6D is a graph showing that RNFL thickness was monitored by OCT across 15 weeks in both groups, comparing sutured to control eyes for LXB$_4$ and vehicle.
Figure 6E:
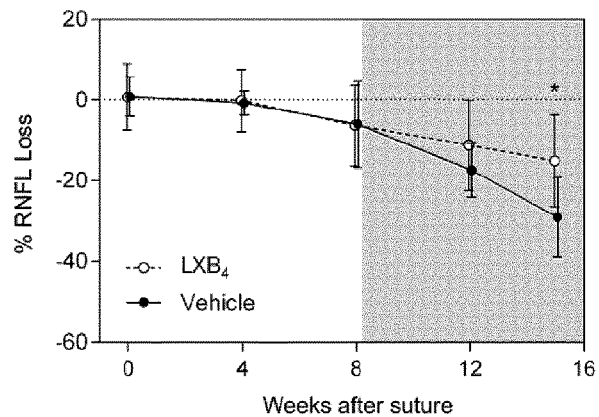
FIG. 6E is a graph showing percent loss compared to control normotensive eyes for LXB$_4$ and vehicle and showing a significant RNFL preservation in the LXB$_4$ group at week 15 (*p<0.05, n-8, bars are S.D., the shaded area indicates the period of treatment).
Figures 12A, 12B:
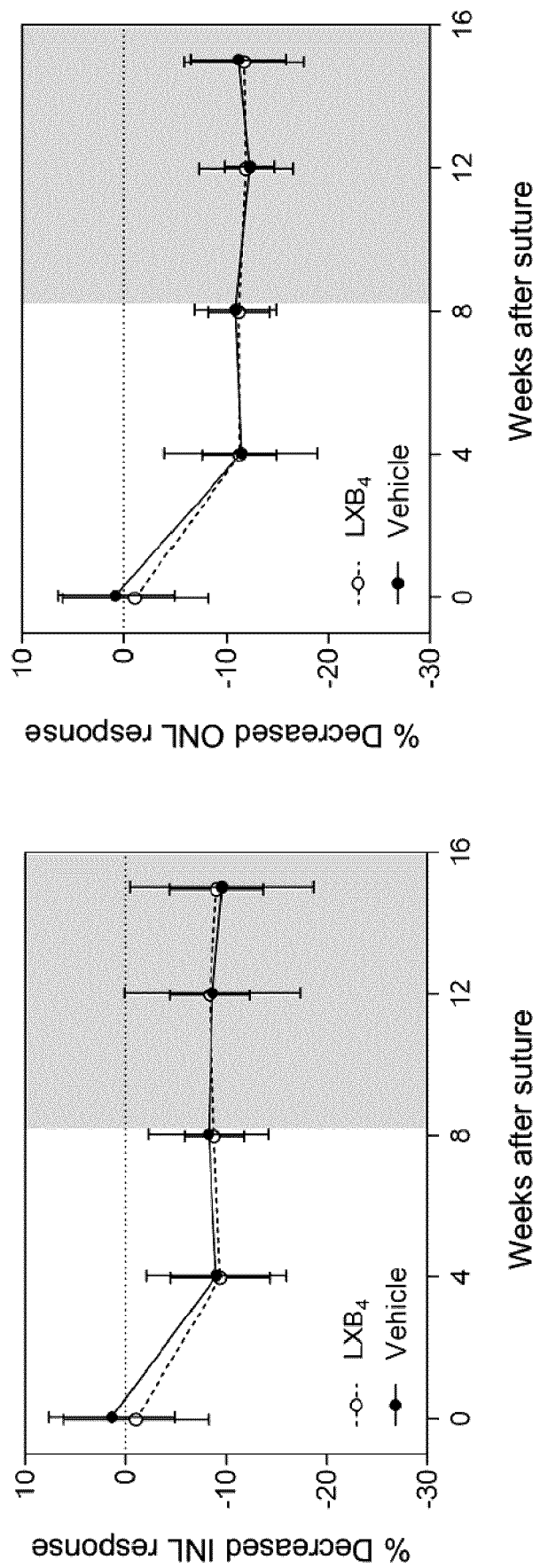
FIG. 12A is a graph that shows that LXB$_4$ treatment had no effect on the mild INL ERG decrease induced by sustained IOP (n=8, bars are S.D., the shaded area represents the period of treatment).
FIG. 12B is a graph that shows that LXB$_4$ treatment had no effect on the mild ONL ERG decrease induced by sustained IOP (n=8, bars are S.D., the shaded area represents the period of treatment).
Figure 13A:
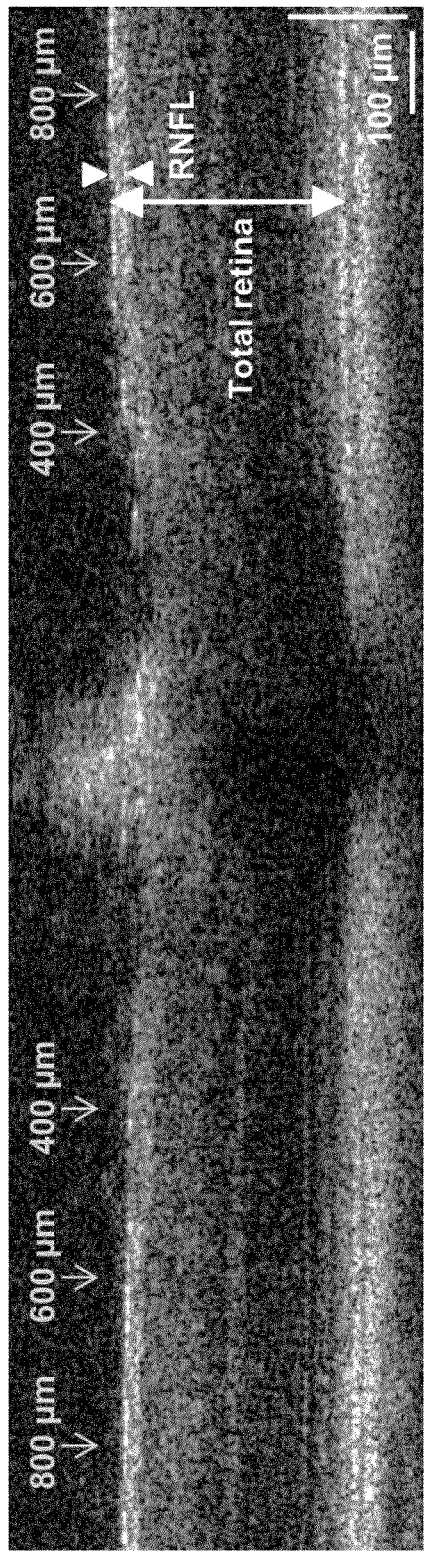
FIG. 13A is a representative OCT b-scan showing RNFL and total retinal measurements, and indicates the sampling protocol (400, 600 and 800 um from ONH in 4 quadrants, an average of 12 readings).
Figure 13C:
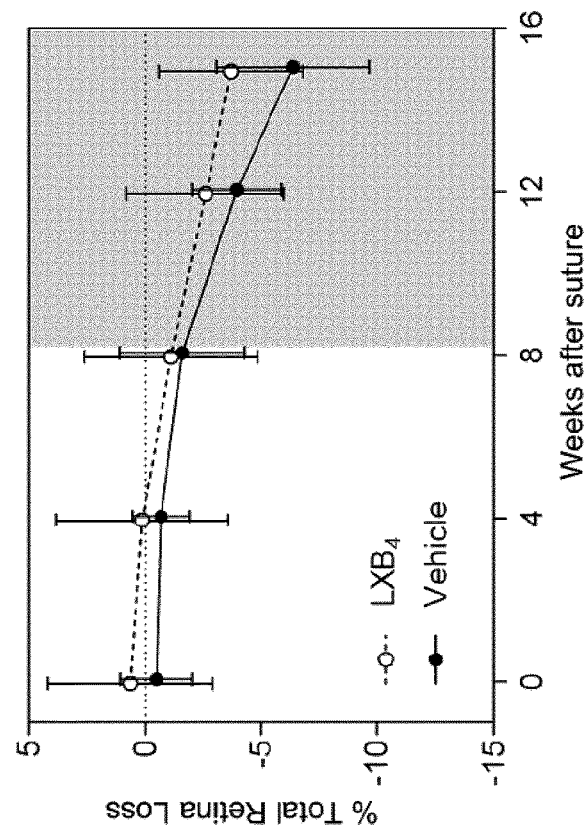
FIG. 13C is a graph showing that a mild decrease in total retinal thickness was not significantly affected by LXB$_4$ treatment compared to vehicle (n=8, bars are S.D., the shaded area represents the period of treatment).
Figure 13B:
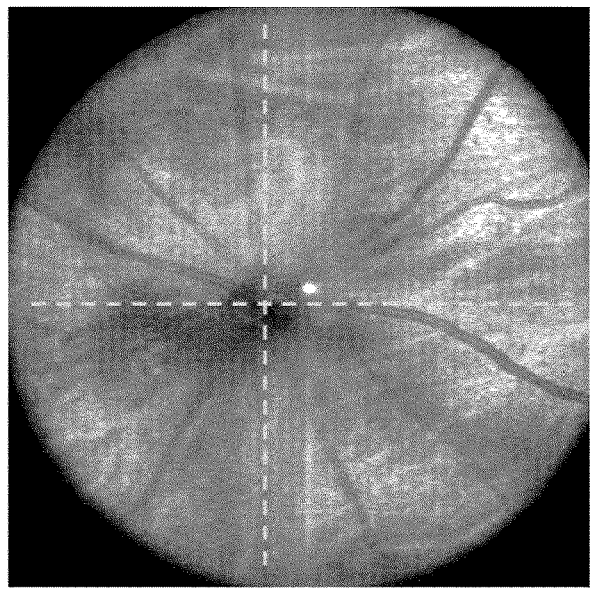
FIG. 13B is a representative retinal en face a-scan.

LXB$_4$ or vehicle treatment of sutured rats was initiated after 8 weeks of elevated IOP, and was delivered on alternate days until week 15. A control group was treated with vehicle only. Additionally, for each rat increased IOP was induced in the unilaterally, with the contralateral eye serving as control. IOP was monitored twice weekly throughout the experiment. As functional and structural endpoints, electroretinograms (ERG) and optical coherence tomography (OCT) were measured at week 0 (before placing the suture), and on weeks 4, 8, and 12, and 15 of elevated IOP. IOP levels in the LXB$_4$ treated group did not differ from the levels in the vehicle treated group (Supplementary FIG. 4), indicating any result was not secondary to an IOP lowering effect. However, by week 12, an RGC-dependent ERG signal, the positive scotopic threshold response (pSTR), showed significant recovery in the LXB$_4$ treated group compared to vehicle (FIG. 6B, FIG. 6C). This recovery increased at week 15, although it did not return to baseline (FIG. 6C). This result was specific to RGCs as in comparison, the a-wave (photoreceptor) and b-wave (bipolar cell) signals showed modest decline and no LXB$_4$ effects (FIG. 12A, FIG. 12B). Similarly, OCT measurement of RNFL thickness, an indicator or RGC axonal loss, showed increasing thinning in the vehicle group, and this loss was partially rescued in the LXB$_4$ treatment group by week 15 (FIG. 6D, FIG. 6E). This result was also specific, as in comparison there was relatively little decline in total retinal thickness, which was not affected by LXB$_4$ treatment (FIG. 13A-FIG. 13C).

Figure 7A:
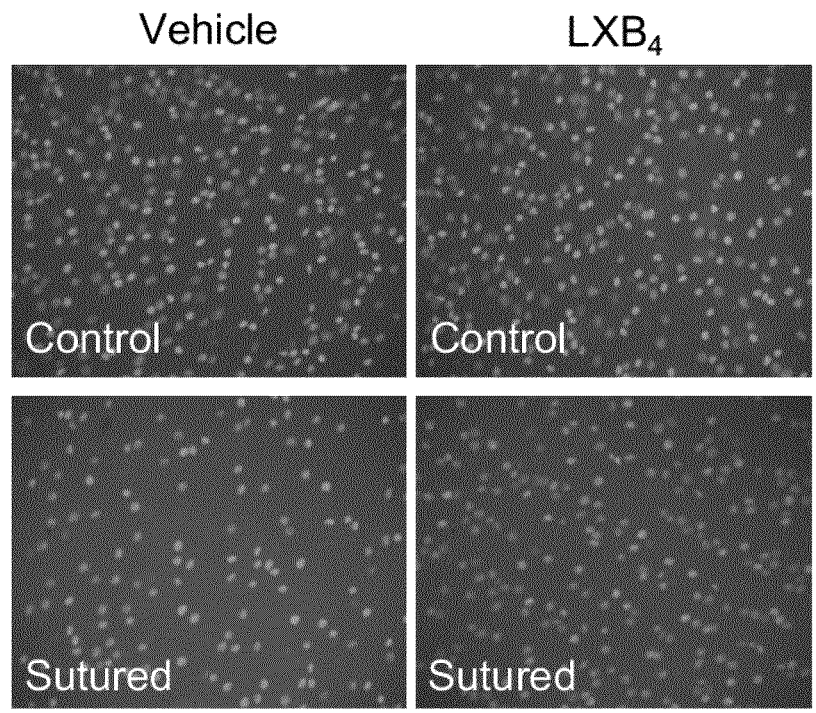
FIGS. 7A and 7B show that therapeutic administration of LXB$_4$ protects RGC survival following chronic IOP injury.
Figure 7B:
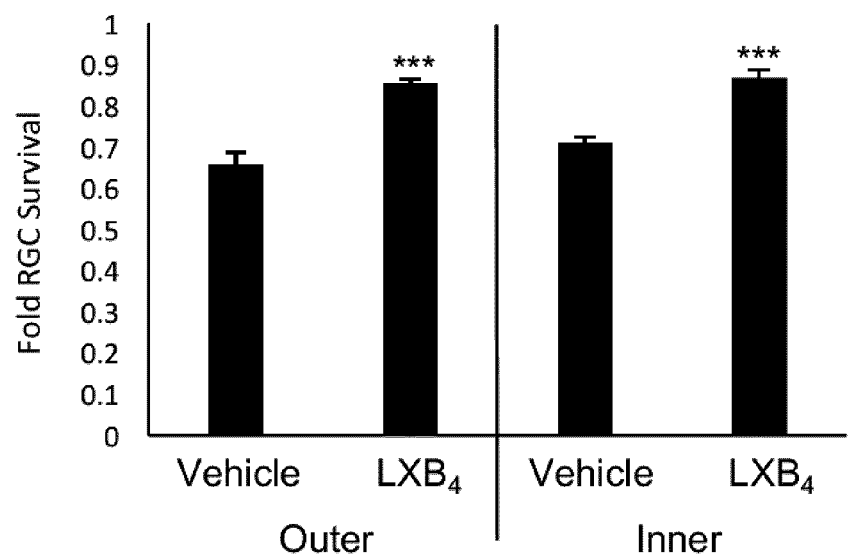
Figure 8A:
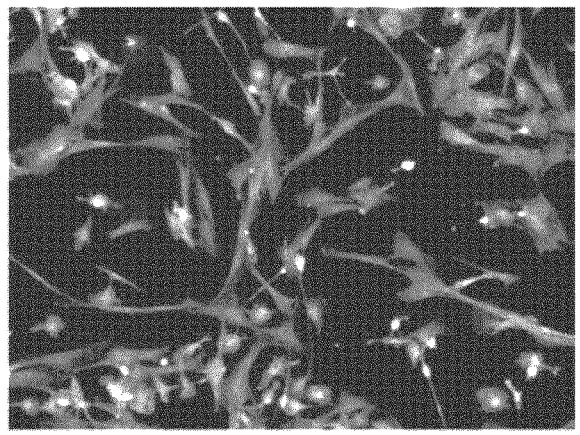
FIG. 8A to 8E are a series of images and blots.
Figure 8B:
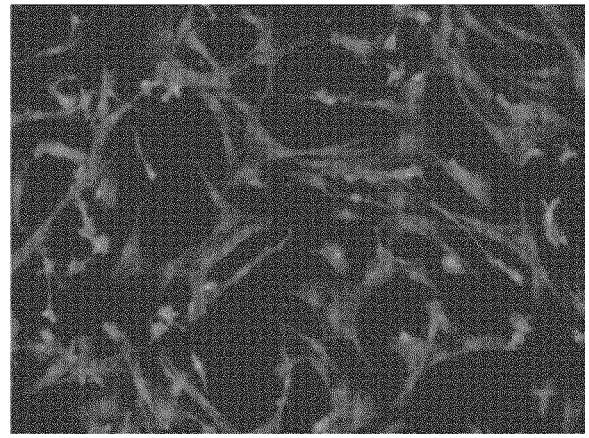
Figure 8C:
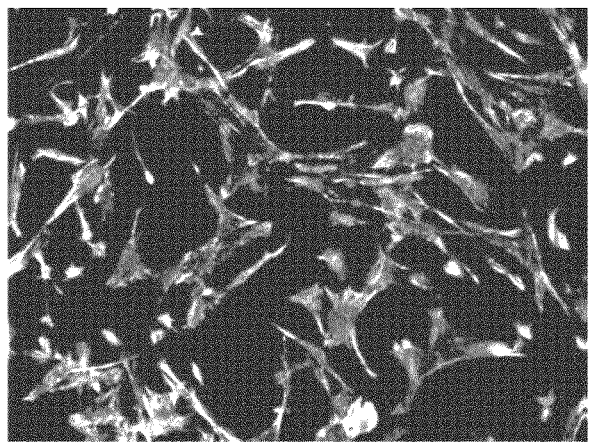
Figure 8D:
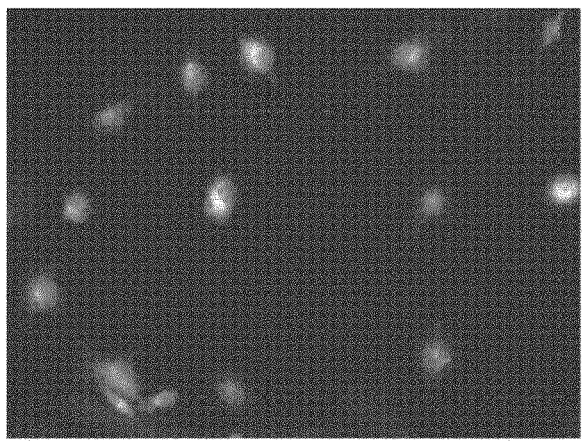
Figure 8E:
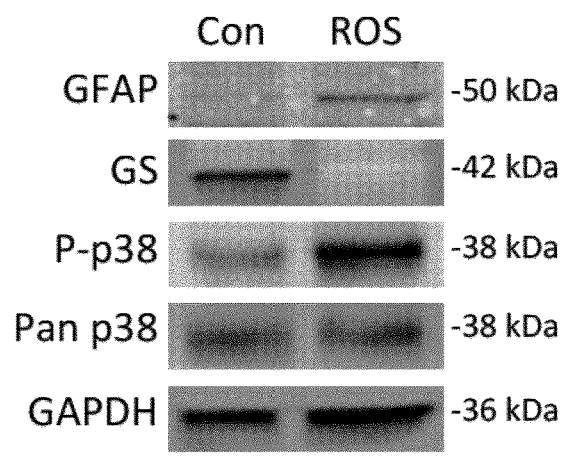

To compare these results to pathological findings animals were euthanized and the retinas flatmounted and stained for BRN3a at week 15. In vehicle eyes there were 35% and 30% fewer BRN3a positive RGCs in sutured eyes compared to contralateral controls in the inner and outer retinas, respectively (FIG. 7A-FIG. 7B). Consistent with the ERG and OCT findings, there was a significant rescue of RGCs in both regions of LXB$_4$ treated retinas compared to vehicle (FIG. 7A-FIG. 7B). Together, these data demonstrate substantial recovery of RGC function and increased survival following therapeutic administration of LXB$_4$ in a model of sustained, IOP-induced optic neuropathy.

Discussion

This study provides the first evidence that LXA$_4$ and LXB$_4$ are astrocyte released neuroprotective factors in acute and chronic injury models. The most established protective factors in the CNS are relatively stable target derived neurotrophic proteins (75-77). However, the endogenous role and regulation of labile small molecule protective factors in the context of neuronal damage and inflammation are much less understood. Dysregulation of SPMs has been implicated in models of neuroinflammation, including Alzheimer's disease, stroke, and age related macular degeneration (19, 20). However, most SPM actions have been linked to their established anti-inflammatory and pro-resolving activities. To the inventor's knowledge, only the structurally distinct DHA derivative, NPD1, has been shown to have direct neuroprotective actions (21-23, 78). The lipoxins, $LXA_4$ and $LXB_4$, were the first identified SPMs and remain the only arachidonic acid-derived mediators. Importantly, arachidonic acid is the most abundant substrate for lipoxygenase and cyclooxygenase enzymes in most cells and tissues by several orders of magnitude. $LXA_4$ anti-inflammatory activities mediate protective outcomes in models of Alzheimer's disease (AD), stroke, and neuropathic pain (29-32). However, the formation and secretion of lipoxins by astrocytes, and their direct neuronal actions, have not been reported.

The findings identify direct neuroprotection and potentially neurotrophic roles as a novel lipoxin activity. In particular, $LXB_4$ was consistently more potent in the neuroprotective experiments than $LXA_4$ in vitro, with a marked rescue of neurite survival. Unlike $LXA_4$, the formation and bioactions of $LXB_4$ have not been fully investigated, likely due to the lack of an established receptor for $LXB_4$, making experimental and therapeutic strategies more challenging. Inhibition of receptors for two related molecules, the $LXA_4$ receptor (FPR2) or RvD2 receptor (GPR18), were insufficient to block the protective $LXB_4$ activity. These results suggest that $LXB_4$ neuroprotective signaling may be distinct from $LXA_4$, and is not mediated via the recently identified receptor for its DHA structural homolog, RvD2 (74). Studies, investigating $LXB_4$ signaling are limited but it triggers potent non-phlogistic activation of macrophages without calcium mobilization (28).

The observations stem from experiments directed at the regulation of protective astrocyte activities. Astrocytes are critical support cells of the CNS. Under normal conditions they maintain a host of homeostatic support functions. However, in response to insult, they transition to para-inflammatory reactive states, which can have both positive and negative influences on neighboring neurons (79-81). The data is consistent with a homeostatic role for lipoxins in retinal astrocytes. It is shown that $LXB_4$ is constitutively produced in the inner retina, but the synthetic pathway is rapidly downregulated upon injury. This regulation suggests a model in which $LXB_4$ coordinates a constitutive neuroprotective or neurotrophic signal, and simultaneously maintains an anti-tone that raises the threshold for triggering neuroinflammation. This mechanism would complement a classification recently proposed by Liddelow et al (82), in which reactive astrocytes can transition to toxic or protective A1 or A2 states following injury or during neurodegeneration.

Based on the promising data for $LXB_4$, a challenging therapeutic test in a 15-week model of chronic glaucoma based on sustained elevated IOP was performed. As evidence of compromised RGC function in this model is not evident until week 8, dosing began at this time point, running the risk that substantial subthreshold damage had already occurred. Yet, $LXB_4$ treatment was significantly efficacious in longitudinal measures used clinically, as well as by pathological assessment.

Glaucoma is a leading cause of vision loss and blindness worldwide, and shares many facets with related neurodegenerative diseases throughout the CNS (10, 12, 86). Common features include early astrocyte reactivity, metabolic dysfunction, neurotrophic factor deprivation, oxidative stress, and parainflammation. Yet, glaucoma is often asymptomatic in early stages, and there are no neuroprotective treatments for the associated RGC degenerations (87). Aging and increased intraocular pressure (IOP) are major risk factors (88-90). However, many patients do not present with elevated IOP, and despite effective pressure reduction, nearly all patients will eventually progress (89, 91, 92). Therefore, new treatment strategies are desperately needed. The efficacious results with $LXB_4$ treatment in a chronic IOP-dependent glaucoma model extend beyond the standard of care offered by current IOP lowering strategies by directly targeting the pathological neurodegenerative cascade in the retina, without affecting IOP. Therefore, this strategy may treat all forms of the disease. Additionally, lipoxins were also neuroprotective in HT22 cells, a hippocampal neuronal cell line, suggesting that the neuroprotective effects may extend to other compartments of the brain. As metabolic, excitotoxic, and biomechanical injuries are also involved in other neurodegenerative processes, such as stroke, Alzheimer's disease, and Parkinson's disease, these results suggest lipoxins and lipoxin analogues may be neuroprotective in CNS disease contexts. Further supporting this, is data showing that lipoxins are effective in protecting primary cortical neurons and a dopaminergic cell line SH-SY5Y cell line.

Example 3

Additional experiments were conducted using the methods described in Example 2.

Figure 14:
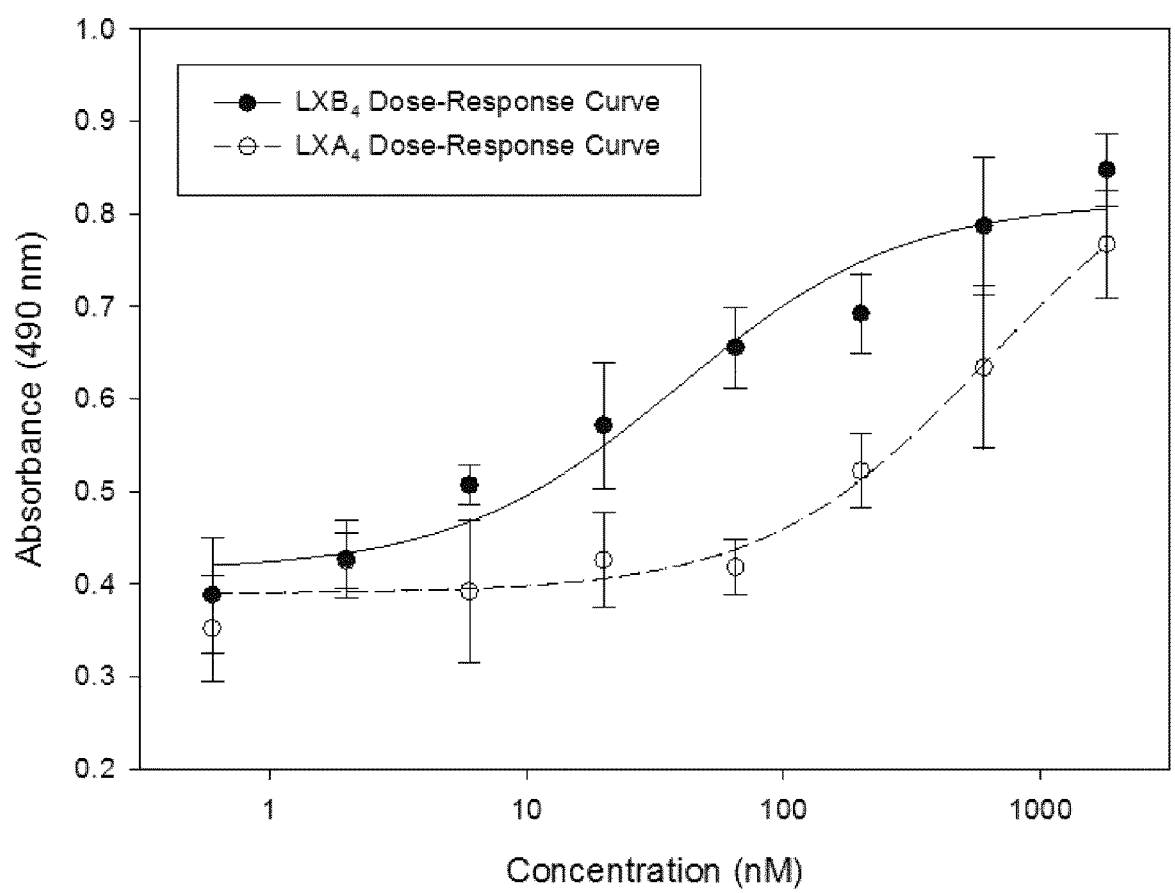
FIG. 14 is a graph that shows Lipoxin neuroprotection is dose responsive.

As shown in FIG. 14 lipoxin neuroprotection is dose responsive. Dose responses were generated for $LXA_4$ (open circles) and $LXB_4$ (closed circles) in HT22 cells exposed to glutamate stress, followed by nonlinear regression analyses. The calculated $EC_{50}$ for $LXA_4$ was 631.0 nM with an efficacy of 0.89, and $LXB_4$ was 39.2 nM with an efficacy of 0.81 (n=3/point, bars are S.E.M.).

Figure 15A:
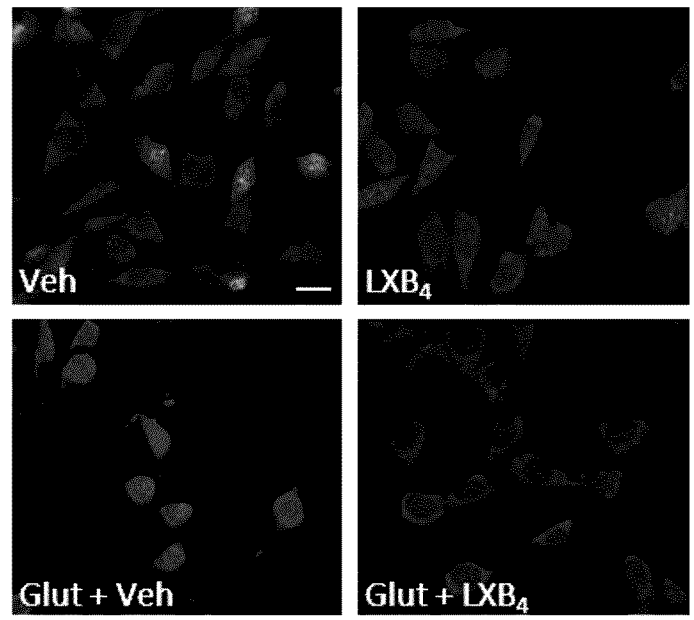
FIG. 15A and FIG. 15B is a series of images and a graph that show LXB$_4$ treatment inhibits glutamate induced mitochondrial activity.
Figure 15B:
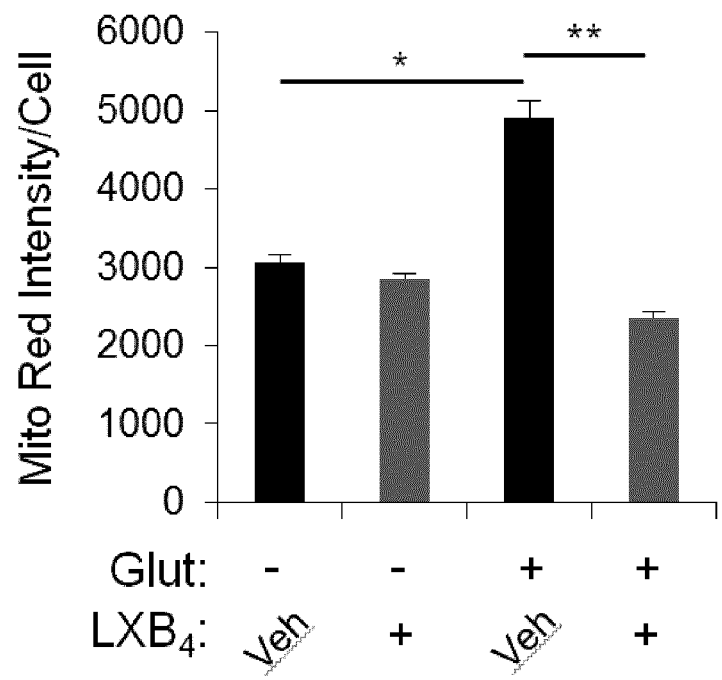

The mechanism of protection was investigated. $LXB_4$ treatment was found to inhibit glutamate induced mitochondrial activity. FIG. 15A shows representative images of HT22 cells treated with vehicle or 1 μM $LXB_4$ and then challenged with glutamate, followed by staining with MitoTracker Red. $LXB_4$ blocked the glutamate induced increase in mitochondrial membrane potential, indicated by increased fluorescence (Scale bar=20 μm). FIG. 15B show quantification of fluorescent intensity per cell (n=3, *p<0.05, **p<0.01, bars represent S.E.M.).

Figure 16B:
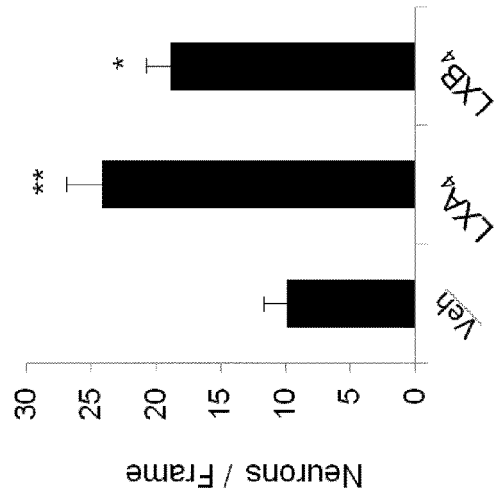
FIG. 16A to FIG. 16D are series of images and graphs that show Lipoxins rescue RGC survival and reduce neurite disintegration under serum deprivation.
Figure 16D:
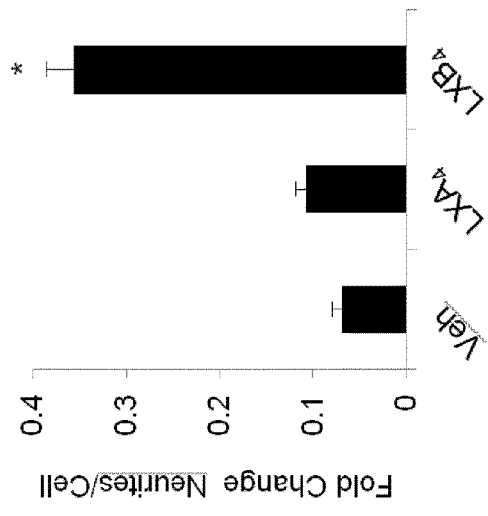
Figure 16A:
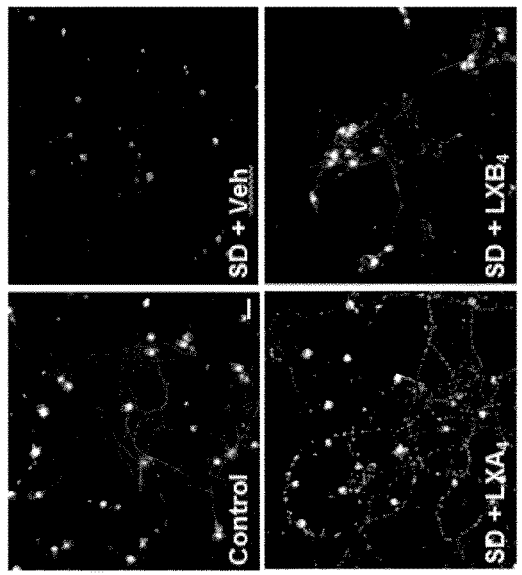
Figure 16C:
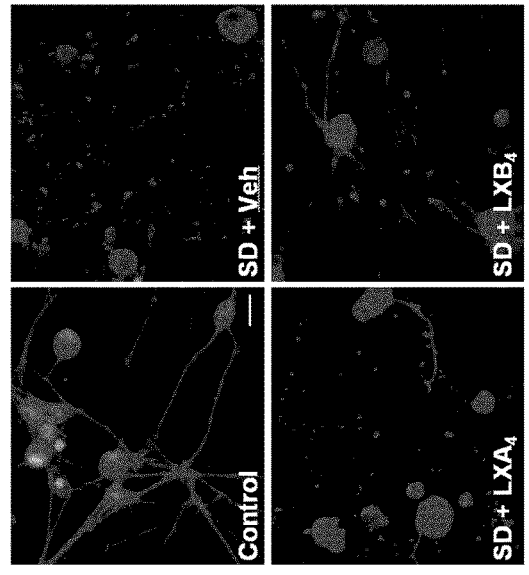

Experiments were also conducted to assess the effects of lipoxins on neural cell survival and neurite degeneration. Lipoxins rescued RGC survival and reduced neurite disintegration under serum deprivation. FIG. 16A shows primary RGCs labeled with β3-tubulin RGC are dramatically reduced after 48 hours of serum and supplement deprivation (SD+Veh), but the loss is rescued by treatment with 1 μM $LXA_4$ or $LXB_4$ (bar indicates 20 μm). FIG. 16B shows quantification of neuron survival following SD demonstrates significant rescue with $LXA_4$ or $LXB_4$ treatment (*p<0.05, **p<0.01, n=3, bars are S.E.M.). FIG. 16C shows neurite degeneration following SD was strongly rescued by $LXB_4$, but not $LXA_4$ (bar indicates 20 μm). FIG. 16D shows quantification of intact neurite ratio shows significant rescue by $LXB_4$ (*p<0.05, n=3, bars are S.E.M.).

Figure 17:
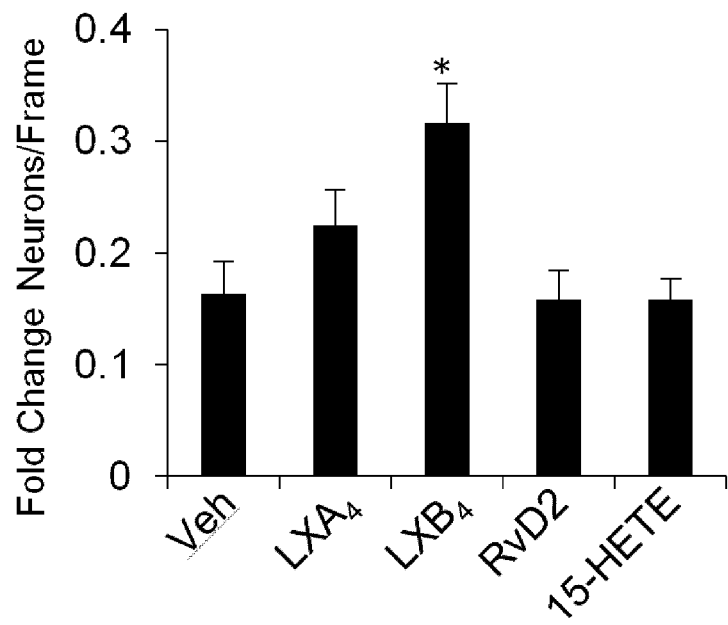
FIG. 17 is a graph showing LXB$_4$ treatment rescues primary cortical neurons.

FIG. 17 is a graph showing $LXB_4$ treatment rescues primary cortical neurons. Quantification of neuron number following oxidative stress from the redox cycling compound paraquat in primary cortical neurons. LXA$_4$ and LXB$_4$ have activities in primary cortical neurons, compared to the related RvD2 and 15-HETE, which show no protection (n=5, *p<0.05, bars represent S.E.M.)

Figure 18A:
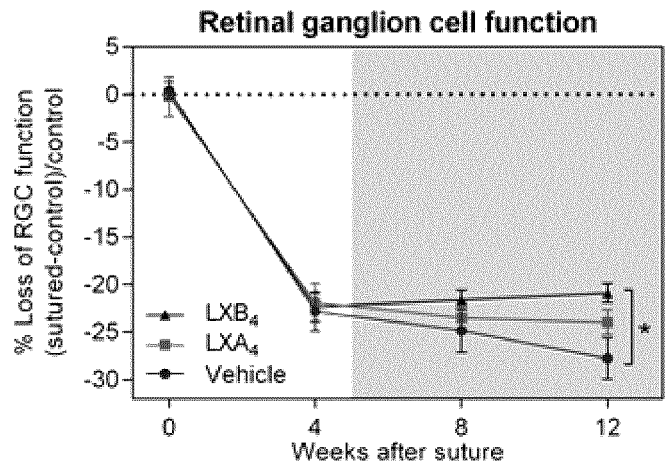
FIG. 18A to FIG. 18C are graphs showing LXA$_4$ and LXB$_4$ treatment are efficacious in a mouse chronic glaucoma model.
Figure 18B:
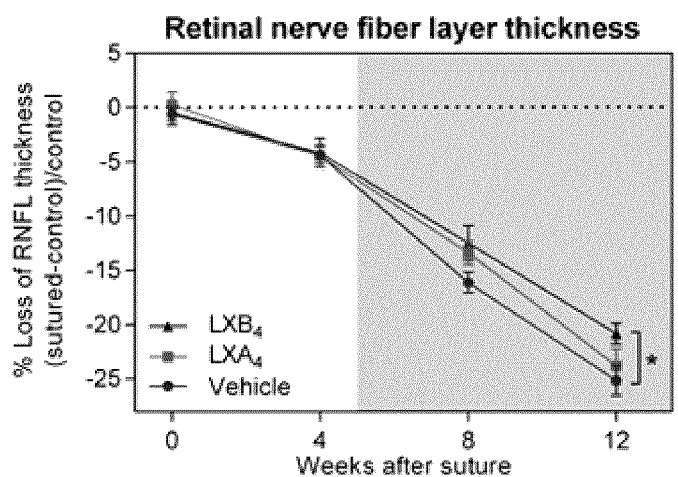
Figure 18C:
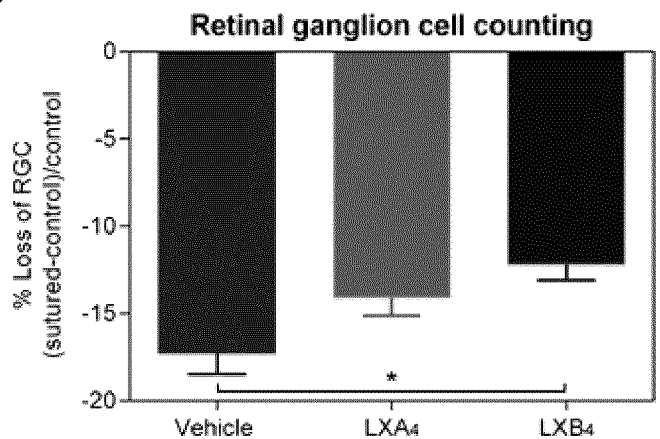

LXA$_4$ and LXB$_4$ treatment were assessed and found to be efficacious in a mouse chronic glaucoma model. Chronic ocular hypertension was induced in weaned male C57BL/6 mice using a monocular circumlimbal suture. From week 5, they were treated with either PBS vehicle, LXA$_4$ or LXB$_4$ (0.1 µg/µL, locally and systemically, every other day) (shaded areas). Retinal function (electroretinogram) and structure (optical coherence tomography) were measured weekly in all groups for 12 weeks. At the end of 12 weeks, animals were euthanized and retinal ganglion cell (RGC) counts were analyzed on retinal flatmounts by RBPMS immunostaining. FIG. 18A shows at week 12, RGC function (pSTR) was reduced by −27.8±2.1% in the vehicle group, but only −24.0±1.3% in the LXA$_4$ group (p=0.29) and −20.9±1.0% in the LXB$_4$ group (*p<0.01), representing a significant functional effect. FIG. 18B shows retinal nerve fiber layer (RNFL) thickness was reduced by −25.2±1.4% in the vehicle group compared to −23.8±1.6% in the LXA$_4$ group (p>0.99) and −20.9±1.0% in the LXB$_4$ group (*p<0.05). FIG. 18C shows loss of RGC in the vehicle group was −17.2±1.2%, −14.1±1.0% for the LXA$_4$ group (p=0.13) and −12.2±0.9% for the LXB$_4$ group (*p<0.01). (n=10 per group, bars represent S.E.M.).

Figure 19:
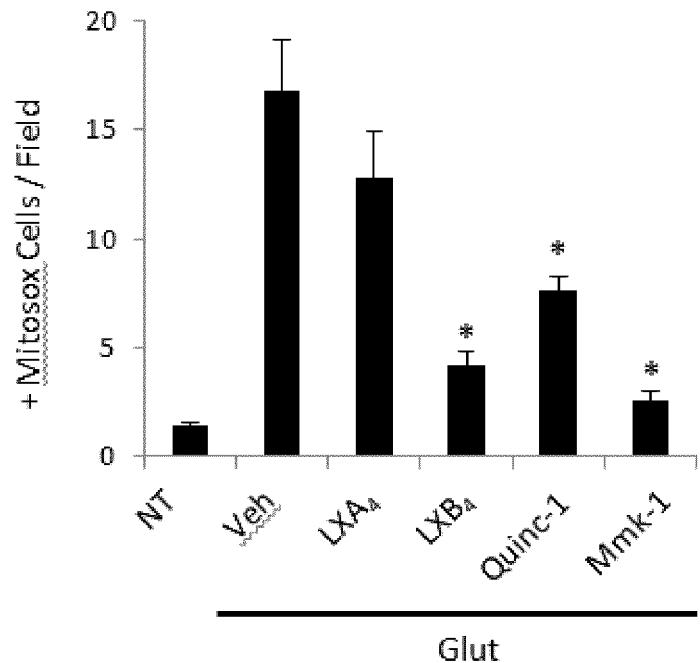
FIG. 19 is a graph showing that lipoxins and FPR2 agonists reduce mitochondrial oxidative stress induced by glutamate treatment.

Lipoxins and FPR2 agonists were found to reduce mitochondrial oxidative stress. HT22 cells challenged with glutamate were then assayed for mitochondrial oxidative stress using the Mitosox reagent, in combination with 1 µM LXA$_4$, LXB$_4$, and the LXA$_4$ receptor ALX/FPR2 agonists Quinc-1 and Mmk-1. (n=3, *p<0.05 compared to vehicle (veh), bars represent S.E.M.) D) Lipoxins also stabilize mitochondria in dopaminergic SH-SY5Y cells in response to paraquat (PQ) induced oxidative stress (n=3, *p<0.05 compared to vehicle, bars represent S.E.M.). The results are shown in FIG. 19.

Figure 20:
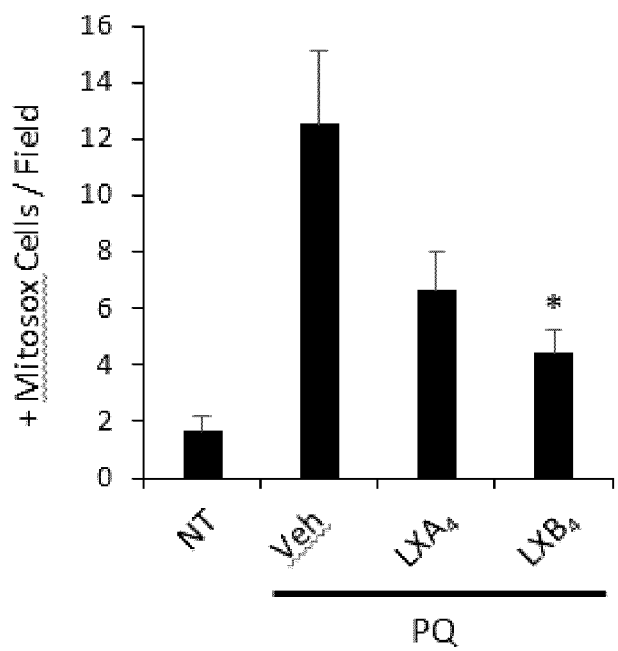
FIG. 20 is a graph showing lipoxins and rescue mitochondrial oxidative stress in dopaminergic neurons induced by PQ treatment.

As shown in FIG. 20, it was found that lipoxins and rescue mitochondrial oxidative stress in dopaminergic neurons. LXA$_4$ and LXB$_4$ stabilize mitochondria in dopaminergic SH-SY5Y cells in response to paraquat (PQ) induced oxidative stress (n=3, *p<0.05 compared to vehicle, bars represent S.E.M.)

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

1. Chung W S, Welsh C A, Barres B A, and Stevens B. Do glia drive synaptic and cognitive impairment in disease? *Nat Neurosci*. 2015; 18(11):1539-45.
2. Doty K R, Guillot-Sestier M V, and Town T. The role of the immune system in neurodegenerative disorders: Adaptive or maladaptive? *Brain Res*. 2015; 1617(155-73.
3. Klein R S, Garber C, and Howard N. Infectious immunity in the central nervous system and brain function. *Nat Immunol*. 2017; 18(2):132-41.
4. Xu H, Chen M, and Forrester J V. Para-inflammation in the aging retina. *Prog Retin Eye Res*. 2009; 28(5):348-68.
5. Mariga A, Mitre M, and Chao M V. Consequences of brain-derived neurotrophic factor withdrawal in CNS neurons and implications in disease. *Neurobiol Dis*. 2017; 97(Pt B):73-9.
6. Levi-Montalcini R, and Booker B. Destruction of the Sympathetic Ganglia in Mammals by an Antiserum to a Nerve-Growth Protein. *Proc Natl Acad Sci USA*. 1960; 46(3):384-91.
7. Cohen-Cory S, and Fraser S E. Effects of brain-derived neurotrophic factor on optic axon branching and remodelling in vivo. *Nature*. 1995; 378(6553):192-6.
8. Hofer M M, and Barde Y A. Brain-derived neurotrophic factor prevents neuronal death in vivo. *Nature*. 1988; 331(6153):261-2.
9. Johnson T V, and Tomarev S I. Rodent models of glaucoma. *Brain Res Bull*. 2010; 81(2-3):349-58.
10. Sivak J M. The aging eye: common degenerative mechanisms between the Alzheimer's brain and retinal disease. *Invest Ophthalmol Vis Sci*. 2013; 54(1):871-80.
11. Weinreb R N, Leung C K, Crowston J G, Medeiros F A, Friedman D S, Wiggs J L, and Martin K R. Primary open-angle glaucoma. *Nat Rev Dis Primers*. 2016; 2(16067.
12. Tham Y C, Li X, Wong T Y, Quigley H A, Aung T, and Cheng C Y. Global prevalence of glaucoma and projections of glaucoma burden through 2040: a systematic review and meta-analysis. *Ophthalmology*. 2014; 121 (11):2081-90.
13. Almasieh M, Wilson A M, Morquette B, Cueva Vargas J L, and Di Polo A. The molecular basis of retinal ganglion cell death in glaucoma. *Prog Retin Eye Res*. 2012; 31(2):152-81.
14. Calkins D J, Pekny M, Cooper M L, Benowitz L, Lasker IIoA, and Glaucomatous Neurodegeneration P. The challenge of regenerative therapies for the optic nerve in glaucoma. *Exp Eye Res*. 2017.
15. Hernandez M R, Miao H, and Lukas T. Astrocytes in glaucomatous optic neuropathy. *Prog Brain Res*. 2008; 173(353-73.
16. Bennett M, and Gilroy D W. Lipid Mediators in Inflammation. *Microbiol Spectr*. 2016; 4(6).
17. Gronert K. Lipid autacoids in inflammation and injury responses: a matter of privilege. *Mol Interv*. 2008; 8(1): 28-35.
18. Serhan C N. Pro-resolving lipid mediators are leads for resolution physiology. *Nature*. 2014; 510(7503):92-101.
19. Gordon W C, and Bazan N G. Mediator lipidomics in ophthalmology: targets for modulation in inflammation, neuroprotection and nerve regeneration. *Curr Eye Res*. 2013; 38(10):995-1005.
20. Serhan C N, Dalli J, Colas R A, Winkler J W, and Chiang N. Protectins and maresins: New pro-resolving families of mediators in acute inflammation and resolution bioactive metabolome. *Biochimica et biophysica acta.* 2015; 1851 (4):397-413.
21. Bazan N G. Neuroprotectin D1 (NPD1): a DHA-derived mediator that protects brain and retina against cell injury-induced oxidative stress. *Brain Pathol.* 2005; 15(2):159-66.
22. Calandria J M, Asatryan A, Balaszczuk V, Knott E J, Jun B K, Mukherjee P K, Belayev L, and Bazan N G. NPD1-mediated stereoselective regulation of BIRC3 expression through cREL is decisive for neural cell survival. *Cell Death Differ.* 2015; 22(8):1363-77.
23. Mukherjee P K, Marcheselli V L, Serhan C N, and Bazan N G. Neuroprotectin D1: a docosahexaenoic acid-derived docosatriene protects human retinal pigment epithelial cells from oxidative stress. *Proc Natl Acad Sci USA.* 2004; 101(22):8491-6.
24. Romano M, Cianci E, Simiele F, and Recchiuti A. Lipoxins and aspirin-triggered lipoxins in resolution of inflammation. *Eur J Pharmacol.* 2015; 760(49-63.
25. Ryan A, and Godson C. Lipoxins: regulators of resolution. *Curr Opin Pharmacol.* 2010; 10(2):166-72.
26. Serhan C N, Hamberg M, and Samuelsson B. Lipoxins: novel series of biologically active compounds formed from arachidonic acid in human leukocytes. *Proc Natl Acad Sci USA.* 1984; 81(17):5335-9.
27. Maddox J F, Hachicha M, Takano T, Petasis N A, Fokin V V, and Serhan C N. Lipoxin A4 stable analogs are potent mimetics that stimulate human monocytes and THP-1 cells via a G-protein-linked lipoxin A4 receptor. *J Biol Chem.* 1997; 272(11):6972-8.
28. Romano M, Maddox J F, and Serhan C N. Activation of human monocytes and the acute monocytic leukemia cell line (THP-1) by lipoxins involves unique signaling pathways for lipoxin A4 versus lipoxin B4: evidence for differential Ca2+ mobilization. *Journal of immunology.* 1996; 157(5):2149-54.
29. Czapski G A, Czubowicz K, Strosznajder J B, and Strosznajder R P. The Lipoxygenases: Their Regulation and Implication in Alzheimer's Disease. *Neurochem Res.* 2016; 41(1-2):243-57.
30. Martini A C, Forner S, Bento A F, and Rae G A. Neuroprotective effects of lipoxin A4 in central nervous system pathologies. *Biomed Res Int.* 2014; 2014 (316204.
31. Tassoni D, Kaur G, Weisinger R S, and Sinclair A J. The role of eicosanoids in the brain. Asia Pac *J Clin Nutr.* 2008; 17 Suppl 1(220-8.
32. Wang X, Zhu M, Hjorth E, Cortes-Toro V, Eyjolfsdottir H, Graff C, Nennesmo I, Palmblad J, Eriksdotter M, Sambamurti K, et al. Resolution of inflammation is altered in Alzheimer's disease. *Alzheimers Dement.* 2015; 11(1):40-50 el-2.
33. Gronert K. Resolution, the grail for healthy ocular inflammation. *Exp Eye Res.* 2010; 91(4):478-85.
34. Sapieha P, Stahl A, Chen J, Seaward M R, Willett K L, Krah N M, Dennison R J, Connor K M, Aderman C M, Liclican E, et al. 5-Lipoxygenase metabolite 4-HDHA is a mediator of the antiangiogenic effect of omega-3 polyunsaturated fatty acids. *Sci Transl Med.* 2011; 3(69): 69ra12.
35. Das U N. Lipoxins, resolvins, and protectins in the prevention and treatment of diabetic macular edema and retinopathy. *Nutrition.* 2013; 29(1):1-7.
36. Kaviarasan K, Jithu M, Arif Mulla M, Sharma T, Sivasankar S, Das U N, and Angayarkanni N. Low blood and vitreal BDNF, LXA$_4$ and altered Th1/Th2 cytokine balance are potential risk factors for diabetic retinopathy. *Metabolism.* 2015; 64(9):958-66.
37. Tezel G. The role of glia, mitochondria, and the immune system in glaucoma. *Invest Ophthalmol Vis Sci.* 2009; 50(3):1001-12.
38. Tezel G, and Wax M B. Increased production of tumor necrosis factor-alpha by glial cells exposed to simulated ischemia or elevated hydrostatic pressure induces apoptosis in cocultured retinal ganglion cells. *J Neurosci.* 2000; 20(23):8693-700.
39. Lebrun-Julien F, Bertrand M J, De Backer O, Stellwagen D, Morales C R, Di Polo A, and Barker P A. ProNGF induces TNFalpha-dependent death of retinal ganglion cells through a p75NTR non-cell-autonomous signaling pathway. *Proc Natl Acad Sci USA.* 2010; 107(8):3817-22.
40. Tezel G, Li L Y, Patil R V, and Wax M B. TNF-alpha and TNF-alpha receptor-1 in the retina of normal and glaucomatous eyes. *Invest Ophthalmol Vis Sci.* 2001; 42(8): 1787-94.
41. Yuan L, and Neufeld A H. Tumor necrosis factor-alpha: a potentially neurodestructive cytokine produced by glia in the human glaucomatous optic nerve head. *Glia.* 2000; 32(1):42-50.
42. Livne-Bar I, Lam S, Chan D, Guo X, Askar I, Nahirnyj A, Flanagan J G, and Sivak J M. Pharmacologic inhibition of reactive gliosis blocks TNF-alpha-mediated neuronal apoptosis. *Cell death & disease.* 2016; 7(9):e2386.
43. Exler R E, Guo X, Chan D, Livne-Bar I, Vicic N, Flanagan J G, and Sivak J M. Biomechanical insult switches PEA-15 activity to uncouple its anti-apoptotic function and promote erk mediated tissue remodeling. *Exp Cell Res.* 2016; 340(2):283-94.
44. Nahirnyj A, Livne-Bar I, Guo X, and Sivak J M. ROS Detoxification and Proinflammatory Cytokines Are Linked by p38 MAPK Signaling in a Model of Mature Astrocyte Activation. *PLoS One.* 2013; 8(12):e83049.
45. Guo X, Dason E S, Zanon-Moreno V, Jiang Q, Nahirnyj A, Chan D, Flanagan J G, and Sivak J M. PGC-1alpha Signaling Coordinates Susceptibility to Metabolic and Oxidative Injury in the Inner Retina. *Am J Pathol.* 2014.
46. Rogers R S, Dharsee M, Ackloo S, Sivak J M, and Flanagan J G. Proteomics analyses of human optic nerve head astrocytes following biomechanical strain. *Mol Cell Proteomics.* 2012; 11(2):M111 012302.
47. Hassan I R, and Gronert K. Acute changes in dietary omega-3 and omega-6 polyunsaturated fatty acids have a pronounced impact on survival following ischemic renal injury and formation of renoprotective docosahexaenoic acid-derived protectin D1. *Journal of immunology.* 2009; 182(5):3223-32.
48. Murphy R C, Barkley R M, Zemski Berry K, Hankin J, Harrison K, Johnson C, Krank J, McAnoy A, Uhlson C, and Zarini S. Electrospray ionization and tandem mass spectrometry of eicosanoids. *Anal Biochem.* 2005; 346 (1):1-42.
49. Serhan C N, Lu Y, Hong S, and Yang R. Mediator lipidomics: search algorithms for eicosanoids, resolvins, and protectins. *Methods in enzymology.* 2007; 432(275-317.
50. Chen L, Sham C W, Chan A M, Francisco L M, Wu Y, Mareninov S, Sharpe A H, Freeman G J, Yang X J, Braun J, et al. Role of the immune modulator programmed cell death-1 during development and apoptosis of mouse retinal ganglion cells. *Invest Ophthalmol Vis Sci.* 2009; 50(10):4941-8.
51. Harada C, Namekata K, Guo X, Yoshida H, Mitamura Y, Matsumoto Y, Tanaka K, Ichijo H, and Harada T. ASK1 deficiency attenuates neural cell death in GLAST-deficient mice, a model of normal tension glaucoma. *Cell Death Differ.* 2010; 17(11):1751-9.

52. Nishijima K, Ng Y S, Zhong L, Bradley J, Schubert W, Jo N, Akita J, Samuelsson S J, Robinson G S, Adamis A P, et al. Vascular endothelial growth factor-A is a survival factor for retinal neurons and a critical neuroprotectant during the adaptive response to ischemic injury. *Am J Pathol.* 2007; 171(1):53-67.

53. Riesenberg A N, Liu Z, Kopan R, and Brown N L. Rbpj cell autonomous regulation of retinal ganglion cell and cone photoreceptor fates in the mouse retina. *J Neurosci.* 2009; 29(41):12865-77.

54. Guo X, Dason E S, Zanon-Moreno V, Jiang Q, Nahirnyj A, Chan D, Flanagan J G, and Sivak J M. PGC-1alpha signaling coordinates susceptibility to metabolic and oxidative injury in the inner retina. *Am J Pathol.* 2014; 184(4):1017-29.

55. Liu H H, Bui B V, Nguyen C T, Kezic J M, Vingrys A J, and He Z. Chronic ocular hypertension induced by circumlimbal suture in rats. *Invest Ophthalmol Vis Sci.* 2015; 56(5):2811-20.

56. Liu H H, and Flanagan J G. A Mouse Model of Chronic Ocular Hypertension Induced by Circumlimbal Suture. *Invest Ophthalmol Vis Sci.* 2017; 58(1):353-61.

57. Liu H H, He Z, Nguyen C T, Vingrys A J, and Bui B V. Reversal of functional loss in a rat model of chronic intraocular pressure elevation. *Ophthalmic Physiol Opt.* 2017; 37(1):71-81.

58. Biteman B, Hassan I R, Walker E, Leedom A J, Dunn M, Seta F, Laniado-Schwartzman M, and Gronert K. Interdependence of lipoxin A4 and heme-oxygenase in counter-regulating inflammation during corneal wound healing. *FASEB J.* 2007; 21(9):2257-66.

59. Borgeson E, Johnson A M, Lee Y S, Till A, Syed G H, Ali-Shah S T, Guiry P J, Dalli J, Colas R A, Serhan C N, et al. Lipoxin A4 Attenuates Obesity-Induced Adipose Inflammation and Associated Liver and Kidney Disease. *Cell Metab.* 2015; 22(1):125-37.

60. Dunn H C, Ager R R, Baglietto-Vargas D, Cheng D, Kitazawa M, Cribbs D H, and Medeiros R. Restoration of lipoxin A4 signaling reduces Alzheimer's disease-like pathology in the 3xTg-A D mouse model. *Journal of Alzheimer's disease: JAD.* 2015; 43(3):893-903.

61. Fortune B, Bui B V, Morrison J C, Johnson E C, Dong J, Cepurna W O, Jia L, Barber S, and Cioffi G A. Selective ganglion cell functional loss in rats with experimental glaucoma. *Invest Ophthalmol Vis Sci.* 2004; 45(6):1854-62.

62. Exler R E, Guo X, Chan D, Livne-Bar I, Vicic N, Flanagan J G, and Sivak J M. Biomechanical insult switches PEA-15 activity to uncouple its anti-apoptotic function and promote erk mediated tissue remodeling. *Exp Cell Res.* 2015.

63. Ganesh B S, and Chintala S K. Inhibition of reactive gliosis attenuates excitotoxicity-mediated death of retinal ganglion cells. *PLoS One.* 2011; 6(3):e18305.

64. Gomez-Ramos P, and Reinoso-Suarez F Kainic acid prevents peroxidase labeling of retinal ganglion cell bodies in the rat: a possible gate in retrograde axonal transport. *Neurosci Lett.* 1983; 35(1):1-6.

65. Wang Q, Yu S, Simonyi A, Sun G Y, and Sun A Y. Kainic acid-mediated excitotoxicity as a model for neurodegeneration. *Mol Neurobiol.* 2005; 31(1-3):3-16.

66. Lee Y, Park H W, Park S G, Cho S, Myung P K, Park B C, and Lee do H. Proteomic analysis of glutamate-induced toxicity in HT22 cells. *Proteomics.* 2007; 7(2): 185-93.

67. Stanciu M, Wang Y, Kentor R, Burke N, Watkins S, Kress G, Reynolds I, Klann E, Angiolieri M R, Johnson J W, et al. Persistent activation of ERK contributes to glutamate-induced oxidative toxicity in a neuronal cell line and primary cortical neuron cultures. *J Biol Chem.* 2000; 275(16):12200-6.

68. Ivanov I, Kuhn H, and Heydeck D. Structural and functional biology of arachidonic acid 15-lipoxygenase-1 (ALOX15). *Gene.* 2015; 573(1):1-32.

69. Gregor J I, Kilian M, Heukamp I, Kiewert C, Kristiansen G, Schimke I, Walz M K, Jacobi C A, and Wenger F A. Effects of selective COX-2 and 5-LOX inhibition on prostaglandin and leukotriene synthesis in ductal pancreatic cancer in Syrian hamster. *Prostaglandins Leukot Essent Fatty Acids.* 2005; 73(2):89-97.

70. Smith H K, Gil C D, Oliani S M, and Gavins F N. Targeting formyl peptide receptor 2 reduces leukocyte-endothelial interactions in a murine model of stroke. *FASEB J.* 2015; 29(5):2161-71.

71. Fang X, Abbott J, Cheng L, Colby J K, Lee J W, Levy B D, and Matthay M A. Human Mesenchymal Stem (Stromal) Cells Promote the Resolution of Acute Lung Injury in Part through Lipoxin A4. *Journal of immunology.* 2015; 195(3):875-81.

72. He N, Jin W L, Lok K H, Wang Y, Yin M, and Wang Z J. Amyloid-beta(1-42) oligomer accelerates senescence in adult hippocampal neural stem/progenitor cells via formylpeptide receptor 2. *Cell death & disease.* 2013; 4(e924).

73. Maddox J F, and Serhan C N. Lipoxin A4 and B4 are potent stimuli for human monocyte migration and adhesion: selective inactivation by dehydrogenation and reduction. *J Exp Med.* 1996; 183(1):137-46.

74. Chiang N, Dalli J, Colas R A, and Serhan C N. Identification of resolvin D2 receptor mediating resolution of infections and organ protection. *J Exp Med.* 2015; 212(8):1203-17.

75. Reichardt L F. Neurotrophin-regulated signalling pathways. *Philos Trans R Soc Lond B Biol Sci.* 2006; 361 (1473):1545-64.

76. Oppenheim R W, Prevette D, Tytell M, and Homma S. Naturally occurring and induced neuronal death in the chick embryo in vivo requires protein and RNA synthesis: evidence for the role of cell death genes. *Dev Biol.* 1990; 138(1):104-13.

77. Josephy-Hernandez S, Jmaeff S, Pirvulescu I, Aboulkassim T, and Saragovi H U. Neurotrophin receptor agonists and antagonists as therapeutic agents: An evolving paradigm. *Neurobiol Dis.* 2017; 97(Pt B):139-55.

78. Calandria J M, Sharp M W, and Bazan N G. The Docosanoid Neuroprotectin D1 Induces T H-Positive Neuronal Survival in a Cellular Model of Parkinson's Disease. *Cell Mol Neurobiol.* 2015; 35(8):1127-36.

79. Parpura V, Heneka M T, Montana V, Oliet S H, Schousboe A, Haydon P G, Stout R F, Jr., Spray D C, Reichenbach A, Pannicke T, et al. Glial cells in (patho)physiology. *J Neurochem.* 2012; 121(1):4-27.

80. Pekny M, and Pekna M. Astrocyte reactivity and reactive astrogliosis: costs and benefits. *Physiological reviews.* 2014; 94(4):1077-98.

81. Sofroniew M V. Astrogliosis. *Cold Spring Harbor perspectives in biology.* 2014; 7(2).

82. Liddelow S A, Guttenplan K A, Clarke L E, Bennett F C, Bohlen C J, Schirmer L, Bennett M L, Munch A E, Chung W S, Peterson T C, et al. Neurotoxic reactive astrocytes are induced by activated microglia. *Nature.* 2017; 541(7638):481-7.
83. O'Sullivan T P, Vallin K S, Shah S T, Fakhry J, Maderna P, Scannell M, Sampaio A L, Perretti M, Godson C, and Guiry P J. Aromatic lipoxin A4 and lipoxin B4 analogues display potent biological activities. *J Med Chem.* 2007; 50(24):5894-902.
84. Parkinson J F. Lipoxin and synthetic lipoxin analogs: an overview of anti-inflammatory functions and new concepts in immunomodulation. *Inflamm Allergy Drug Targets.* 2006; 5(2):91-106.
85. Claria J, and Serhan C N. Aspirin triggers previously undescribed bioactive eicosanoids by human endothelial cell-leukocyte interactions. *Proc Natl Acad Sci USA.* 1995; 92(21):9475-9.
86. Pascolini D, Mariotti S P, Pokharel G P, Pararajasegaram R, Etya'ale D, Negrel A D, and Resnikoff S. 2002 global update of available data on visual impairment: a compilation of population-based prevalence studies. *Ophthalmic Epidemiol.* 2004; 11(2):67-115.
87. Kwon Y H, Fingert J H, Kuehn M H, and Alward W L. Primary open-angle glaucoma. *The New England journal of medicine.* 2009; 360(11):1113-24.
88. Wilson M R, and Singh K. Intraocular Pressure: Does it Measure Up? *Open Ophthalmol J.* 2009; 3(32-7.
89. Heijl A, Leske M C, Bengtsson B, Hyman L, and Hussein M. Reduction of intraocular pressure and glaucoma progression: results from the Early Manifest Glaucoma Trial. *Archives of ophthalmology.* 2002; 120(10): 1268-79.
90. Caprioli J. Glaucoma: a disease of early cellular senescence. *Invest Ophthalmol Vis Sci.* 2013; 54(14):ORSF60-7.
91. Quigley H A. New paradigms in the mechanisms and management of glaucoma. *Eye.* 2005; 19(12):1241-8.
92. Anderson D R, Drance S M, and Schulzer M. Natural history of normal-tension glaucoma. *Ophthalmology.* 2001; 108(2):247-53.

The invention claimed is:

1. A method for providing neuroprotection from and/or treating a chronic neurodegenerative retinal or brain disorder or condition comprising administering to a subject afflicted with said disorder or condition an effective amount of lipoxin $B_4$ (LXB4) and/or an analog thereof, wherein the chronic retinal or brain neurodegenerative disorder or condition is selected from the group consisting of glaucoma, retinal ischemia, diabetic retinopathy, diabetic macular edema, age related macular degeneration, retinitis pigmentosa, Alzheimer's disease, multiple sclerosis, Parkinson's disease, and amyotrophic lateral sclerosis.

2. The method of claim 1, wherein the chronic neurodegenerative retinal or brain disorder or condition comprises central nervous system neurodegeneration and/or neural cell loss and the effective amount of the $LXB_4$ and/or an analog thereof is administered to the subject in need thereof such that the neurodegeneration and/or neural cell loss is inhibited or prevented.

3. The method of claim 1, wherein the chronic neurodegenerative retinal or brain disorder or condition comprises hippocampal neuron, cortical neuron, optic neuron or retinal ganglion cell neurodegeneration and/or cell loss.

4. The method of claim 1, wherein the chronic neurodegenerative retinal or brain disorder or condition comprises vision loss, reduced vision, or a chronic neurodegenerative retinal or brain disorder.

5. The method of claim 1, wherein the chronic neurodegenerative retinal or brain disorder or condition comprises vision loss or reduced vision.

6. The method of claim 1, wherein the $LXB_4$ and/or an analog thereof is administered by parenteral, intravenous, subcutaneous, intramuscular, intraorbital, ophthalmic, intraocular, intravitreal, intracameral, subtenon, subconjunctival, intraperitoneal, aerosol or oral administration.

7. The method of claim 1, wherein the $LXB_4$ and/or an analog thereof is administered to an eye.

8. The method of claim 7, wherein the $LXB_4$ and/or an analog thereof is administered topically to the eye.

9. The method of claim 1, wherein the concentration of the $LXB_4$ and/or an analog thereof is at least 0.2 nM or 50 nM.

10. The method of claim 1, wherein the concentration of the $LXB_4$ and/or an analog thereof is less than 1 mM.

11. The method of claim 1, wherein the $LXB_4$ and/or an analog thereof is administered in a composition.

12. The method of claim 1, wherein the $LXB_4$ analog is $LXB_4$ methyl ester.

13. The method of claim 1, wherein the $LXB_4$ analog is 15-epi-$LXB_4$.

14. The method of claim 1, wherein the $LXB_4$ analog is benzo-$LXB_4$.

15. The method of claim 1, wherein the glaucoma is or comprises primary open angle glaucoma, secondary open angle glaucoma or normal tension glaucoma.

16. The method of claim 7, wherein the $LXB_4$ and/or analog thereof is administered to the eye by a sustained delivery device, topical gel or ointment, polymer, or intraocular gel, or sustained delivery device implant, polymer, or nanoparticles.

17. The method of claim 16, wherein the sustained delivery device is a contact lens.

* * * * *